US008666475B2

(12) United States Patent
Hirsch

(10) Patent No.: US 8,666,475 B2
(45) Date of Patent: Mar. 4, 2014

(54) IMAGES OF LANGUAGE-SENSITIVE NEUROCIRCUITRY AS A DIAGNOSTIC FOR AUTISM

(75) Inventor: Joy Hirsch, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 13/306,475

(22) Filed: Nov. 29, 2011

(65) Prior Publication Data

US 2012/0143041 A1  Jun. 7, 2012

Related U.S. Application Data

(63) Continuation-in-part of application No. 13/082,078, filed on Apr. 7, 2011, now abandoned, which is a continuation of application No. PCT/US2009/061724, filed on Oct. 22, 2009.

(60) Provisional application No. 61/107,567, filed on Oct. 22, 2008, provisional application No. 61/183,416, filed on Jun. 2, 2009, provisional application No. 61/183,425, filed on Jun. 2, 2009, provisional application No. 61/434,583, filed on Jan. 20, 2011.

(51) Int. Cl.
*A61B 5/05* (2006.01)
*G01V 3/00* (2006.01)

(52) U.S. Cl.
USPC ........... 600/411; 600/410; 600/418; 324/318; 324/317

(58) Field of Classification Search
USPC ............... 600/411, 410, 418; 324/318
See application file for complete search history.

(56) References Cited

U.S. PATENT DOCUMENTS

| 6,463,315 | B1 | 10/2002 | Klingberg et al. |
| 6,539,246 | B2 * | 3/2003 | Heid ............................. 600/410 |
| 7,268,551 | B2 * | 9/2007 | Lange ........................... 324/318 |
| 2002/0103428 | A1 * | 8/2002 | deCharms ..................... 600/410 |
| 2004/0082847 | A1 | 4/2004 | McDermott |
| 2004/0092809 | A1 | 5/2004 | DeCharms |
| 2011/0301495 | A1 | 12/2011 | Hirsch |

FOREIGN PATENT DOCUMENTS

EP  1 946 701  7/2008

OTHER PUBLICATIONS

Lee, Jee Eun et al. Diffusion tensor imaging of white matter in the superior temporal gyrus and temporal stem in autism. Neuroscience Letters 414 (2007) 127-132.*
Boddaert, et al., "Perception of complex sounds in autism: abnormal auditory cortical processing in children", *Am J. Psychiatry*, 161(11):2117-2120 (2004).
Dehaene-Lambertz, et al., Nature and nurture in language acquisition: anatomical and functional brain-imaging studies in infants:, *Trends Neuroscience*, 29(7):367-373 (2006).

(Continued)

*Primary Examiner* — Long V. Le
*Assistant Examiner* — Helene Bor
(74) *Attorney, Agent, or Firm* — Baker Botts LLP

(57) ABSTRACT

The disclosed subject matter provides on ore more imaging techniques during passive auditory stimulation to objectively provide a diagnostic indicator of ASD. These techniques include functional MRI (fMRI), diffusion tensor imaging (DTI) and tractography, and combinations thereof. In one embodiment, a method is disclosed that uniquely provides an objective (imaging) physiological technique to diagnose early autism and to monitor progress following therapeutic intervention.

11 Claims, 23 Drawing Sheets

(56) References Cited

OTHER PUBLICATIONS

Ecker, et al., "Describing the brain in autism in five dimensions—magnetic resonance imaging-assisted diagnosis of autism spectrum disorder using a multiparameter classification approach", *J. Neuroscience*, 30(32):10612-10623 (2010).

Gervais, et al., "Abnormal cortical voice processing in autism", *Nat. Neuroscience*, 7(8):801-802 (2004).

International Search Report for PCT/US2009/061724, dated Dec. 23, 2009 (corresponds to U.S. Appl. Nos. 13/306,475 and 13/082,078).

Jou, et al., "Enlarged right superior temporal gyrus in children and adolescents with autism", *Brain Res.*, 1360:205-212 (2010).

Lai, et al., "Speech stimulation during functional MR imaging as a potential indicator of autism", *Radiology*, 260(2):521-530 (2011).

Muller, et al., "Brain mapping of language and auditory perception in high-functioning autistic adults: a PET study", *J. Autism Dev. Disord.*, 29(1):19-31 (1999).

Rojas, et al., "Planum temporale volume in children and adolescents with autism", *J Autism Dev. Disord.*, 35(4):479-486 (2005).

Vigneau, et al., "Meta-analyzing left hemisphere language areas: phonology, semantics, and sentence processing", *NeuroImage*, 30(4):1414-1432 (2006).

\* cited by examiner

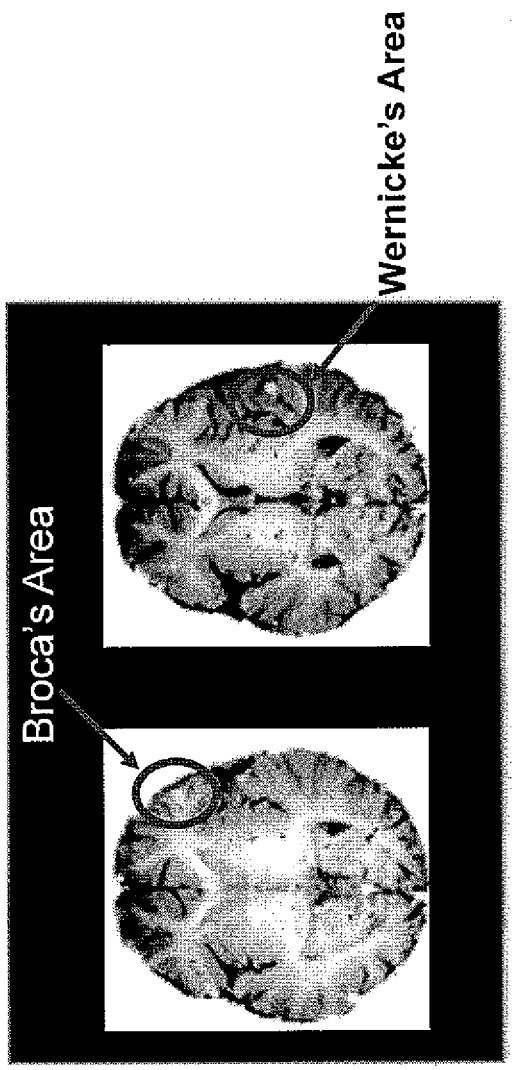
Figure 3a. 6 year old sedated male (normal language function, Neurosurgical planning)

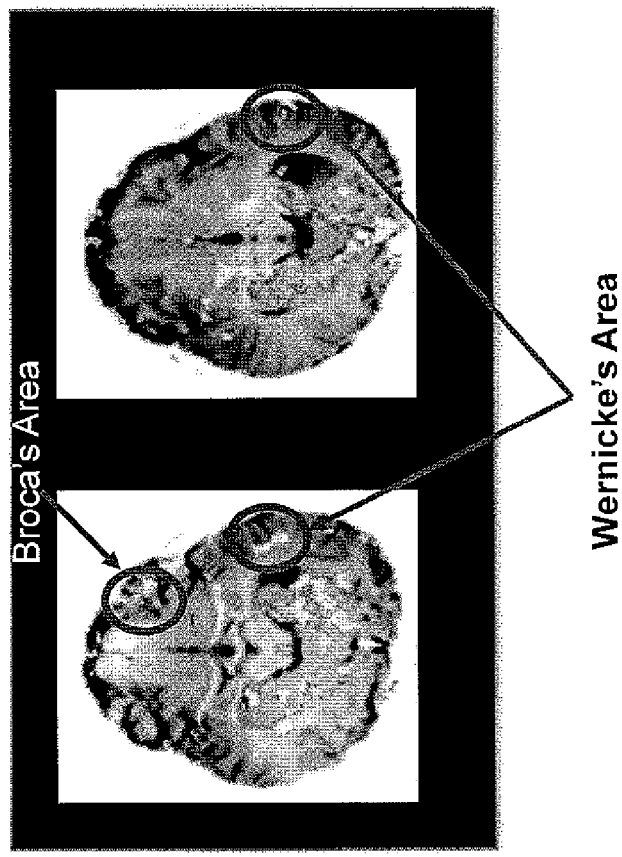
Figure 3b. 4 year old sedated male (normal language function, Neurosurgical planning)

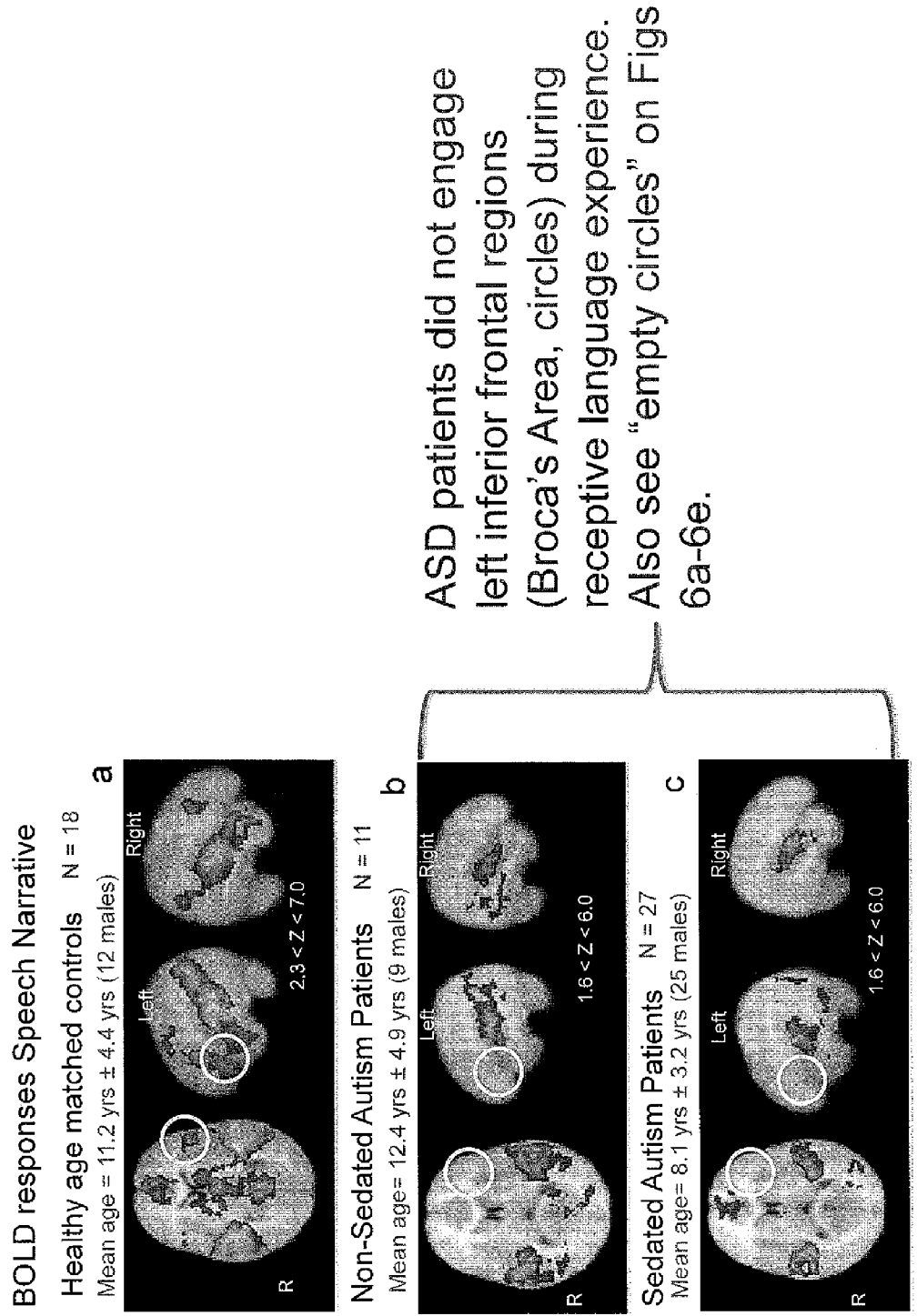
Figure 5: Groups Language Maps fMRI scanning: passive auditory stimulation Stimuli: Audio Recordings and continuous video (a) Spread of activation (b) Amplitude of activation

IMAGES OF LANGUAGE-SENSITIVE NEUROCIRCUITRY AS A DIAGNOSTIC FOR AUTISM

CROSS-REFERENCE TO RELATED APPLICATIONS

This application is a Continuation-in-Part of, and claims priority to, U.S. application Ser. No. 13/082,078, filed Apr. 7, 2011, which is a continuation of International Patent Application No. PCT/US2009/061724, filed on Oct. 22, 2009, which claims priority to U.S. Provisional Application Ser. No. 61/107,567, filed on Oct. 22, 2008, U.S. Provisional Application Ser. No. 61/183,416, filed Jun. 2, 2009, and U.S. Provisional Application Ser. No. 61/183,425, filed Jun. 2, 2009. This application also claims priority to U.S. Provisional Application Ser. No. 61/434,583, filed Jan. 20, 2011. The above-noted applications are hereby explicitly incorporated by reference in their entireties herein.

BACKGROUND

Autism Spectrum Disorder (ASD) is a neurodevelopmental disorder manifested by a spectrum of behavioral anomalies characterized by impaired social interaction and communication, often accompanied by repetitive and stereotypical behavior. The characteristic impairments can be accompanied by mental retardation and/or epilepsy. The condition becomes apparent within the first three years of life and persists into adulthood.

Early behavioral signs of ASD include avoidance of social interaction, lack of eye contact, failure to develop normal conversational skills, and poor language capacities. In a majority of cases, there is no normal period in the child's development (classic autism). Usually, social development is markedly delayed, and language fails to appear or progress normally. Often, these individuals exhibit personality traits that are characterized as "hyper-literal" with a notable predisposition to focus on detail at the expense of abstract meaning.

These characteristics often vary from individual to individual, and, therefore, autism is diagnosed by subjective and behavioral observations. Furthermore, a behavioral-based diagnosis that relies on language and social skills often occurs relatively late in the developmental cycle. Thus, a standardized, neurophysical, diagnostic tool available at early stages of development can facilitate the initiation of therapies at a critical point in time.

It is estimated that one out of every 150 people are affected with ASD, depending on the diagnostic criteria used. The male to female ratio is about four to one. There has been an approximate five-fold increase in the last 10 years in new cases of ASD in the pediatric population of children aged one and a half to six years. These statistics do not reflect the major increase in newly diagnosed cases prior to 1994 when the diagnostic criteria changed.

Although the cause of autism is unknown, recent studies suggest a genetic predisposition to autism associated with disruption of early fetal brain development. There are numerous hypotheses regarding the etiology and pathology of ASD, including a suggested role for immune dysfunction. Autoantibodies against CNS proteins, including neuron-axon filament proteins, cerebellar neurofilaments, myelin basic protein, brain endothelial cells, caudate nucleus, and serotonin receptors have been reported in a subset of ASD patients.

There remains a need for understanding the etiology of ASD and for diagnostic tests predictive of an individual's risk for developing the symptoms indicative of an ASD, allowing for early intervention in the treatment of this neurodevelopmental disorder.

SUMMARY

The presently disclosed subject matter is based on the recent discovery that abnormal brain organization in autism associated with language functions can be detected by imaging methods, alone or in combination, which methods include passive functional MRI (fMRI) and diffusion tensor imaging (DTI), with sedation. These combined methods are described in this application as an early and objective diagnostic for autism using imaging methods to map language-sensitive neurocircuitry. Each of these imaging methods can be applied alone or together as a biological indication of risk for ASD.

In one embodiment, the presently disclosed subject matter is directed to a method of determining whether a test subject suffers from an autism disorder using one or more test subject brain images obtained by one or more imaging techniques selected from the group consisting of functional MRI, DTI, and combinations thereof. The method comprises comparing the one or more test subject brain images to one or more corresponding control subject brain images to identify one or more locations in the test subject brain sensitive to passive auditory stimulation, wherein the one or more identified locations are indicative of an autism spectrum disorder. In certain embodiments, the one or more test subject brain images are obtained from both functional MRI and DTI.

In the presently disclosed subject matter, the passive auditory stimulation can be one or more stimuli selected from the group consisting of speech, reverse speech, instrumental music, song with lyrics, and song without lyrics. The passive auditory stimulation includes alternating periods of audio clips and silence. In certain embodiments, the alternating periods have same time duration. In other embodiments, the alternating periods have different time duration.

In specific embodiments where the imaging technique comprises fMRI, and where the passive auditory stimulation includes speech, the one or more test subject brain images obtained by fMRI include sparse frontal lobe activity, which relates to ASD. In specific embodiments where the imaging technique comprises fMRI, and where the passive auditory stimulation includes speech, the one or more test subject brain images obtained by fMRI include sparse superior temporal gyrus (STG) activity, in both left and right hemispheres, which relates to ASD. In specific embodiments, where the imaging technique comprises DTI, the one or more test subject brain images obtained by DTI include compromised integrity of connectivity from Wernicke's Area to Broca's Area, which relates to ASD. In certain embodiments, the one or more test subject brain images obtained by DTI include a reduced fractional anisotropy value of the arcuate fasciculus, which also relate to ASD. In certain embodiments, the identified locations of activity includes Broca's Area. In other embodiments, the identified locations of activity includes Wernicke's Area.

The presently disclosed subject matter also relates to a method of obtaining MRI brain images of an autistic subject, which steps comprise: (a) selecting one or more prerecorded auditory stimuli selected from the group consisting of speech, reverse speech, instrumental music, song with lyrics, and song without lyrics; (b) selecting a time sequence for periods of alternative auditory stimuli with silence; (c) power-normalizing auditory stimuli with applicable software; (d) providing the prerecorded auditory stimuli to the autistic subject with MR-safe headphones throughout the time sequence; and (e) obtaining MRI images using one or more imaging techniques selected from the group consisting of functional MRI, DTI, and combinations thereof. In certain embodiments, the autistic subject is sedated.

BRIEF DESCRIPTION OF THE DRAWINGS

FIG. 2a illustrates the typical language map observed with fMRI for a sedated 15-month old infant while passively listening to language narratives. Wernicke's Area, the Supplementary Motor Area, and Broca's Area are identified. FIG. 2b depicts the infant's position while undergoing testing.

FIGS. 3a and 3b show functional maps of sedated language-normal children during similar passive listening to recorded speech. FIG. 3a shows the functional mapping of a 6-year old sedated male, and FIG. 3b shows the functional mapping of a 4-year old sedated male.

FIG. 4a shows images of a 24-year old male. FIG. 4b shows images of a 26-year old male. FIG. 4c shows images of a 24-year old male. FIG. 4d shows the imaging of a 30-year old male. FIG. 4e shows images of a 26-year old male. In each Figure, the language-sensitive regions (supplementary motor, Broca's Area and Wernicke's Area) are identified (circles), and the primary language fiber tracts (arcuate fasciculus and uncinate) connecting Broca's and Wernicke's Areas are labeled.

FIGS. 5a through 5c shows the group average (n=5) language maps documenting the across-subject generality of the language system as assessed by passive listening using fMRI for age-matched normal control subjects (FIG. 5a, top row), autism patients (non-sedated) (FIG. 5b, middle row, n–11), and sedated (FIG. 5c, bottom row, n=27).

FIG. 6a shows the imaging of a 6-year old male. FIG. 6b shows the imaging of a 7-year old male. FIG. 6c shows the imaging of a 7-year old male. FIG. 6d shows the imaging of a 7-year old male. FIG. 6e shows the imaging of an 11-year old male.

DETAILED DESCRIPTION

Figure 1:
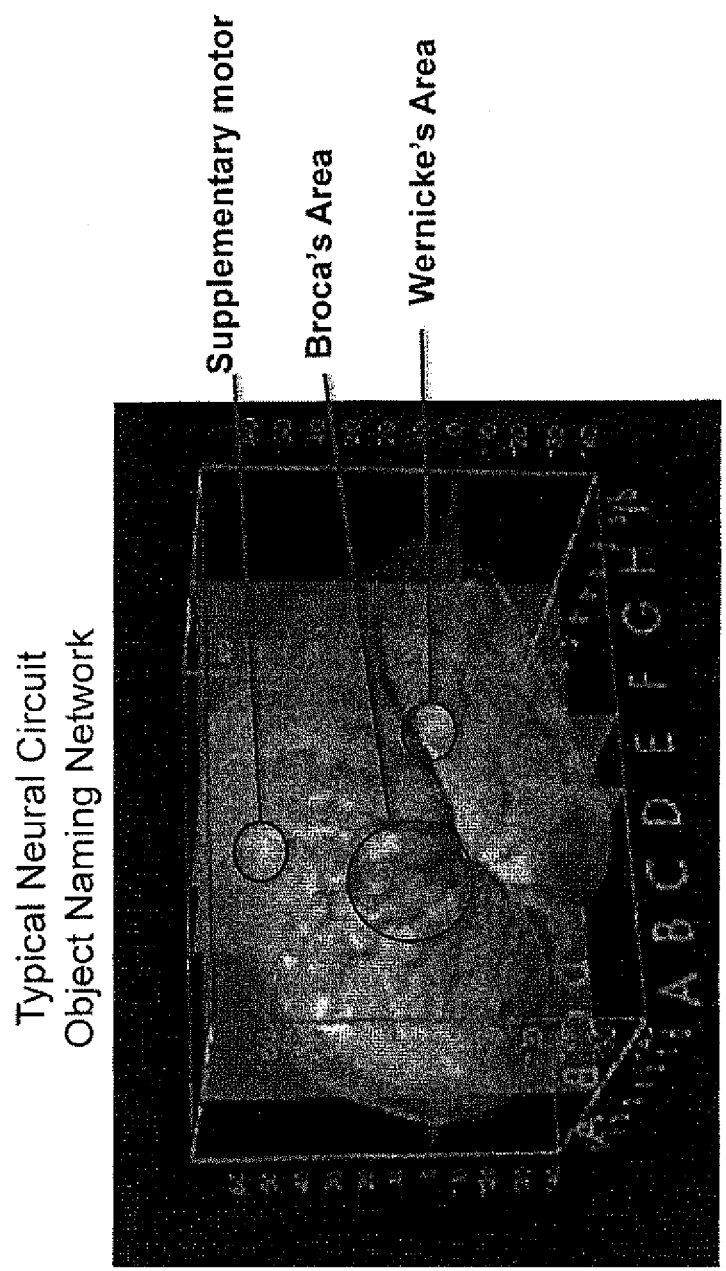
FIG. 1 illustrates a diagram of the brain and neural circuitry related to language functions. Specifically, FIG. 1 identifies the supplementary motor region of the brain as well as Broca's Area and Wernicke's Area.

The presently disclosed subject matter describes an imaging technique based on one or more imaging techniques with passive auditory stimulation, which methods include functional MRI (fMRI), diffusion tensor imaging (DTI), and tractography to objectively provide diagnostic indicators of ASD. These methods uniquely provide objective (imaging) techniques for early diagnosis of autism or ASD. An early diagnosis (by about age 2-3) is essential in order to maximize the benefit of early intervention.

In the presently disclosed subject matter, DTI mapping and fMRI in sedated children with passive auditory stimulation provides one or more diagnostic tests for autism based on anomalous sensitivity and/or connectivity between language sensitive areas. Since autistic children often cannot tolerate awake MRI conditions, conventional fMRI to map language systems is not practical due to the need for task-related responses based on volitional action. Therefore, the present subject matter provides for fMRI during passive listening while sedated. This allows for DTI acquisition, fMRI guided connectivity mapping, comparisons of language maps, and assessments of the integrity of the arcuate fasciculus (AF), which is the neural pathway that connects the posterior temporoparietal junction with the frontal cortex of the brain. It is thought that the AF connects Broca's Area to Wernicke's Area, both of which are involved with language.

Unless otherwise defined, all technical and scientific terms used herein have the same meanings as commonly understood by one of ordinary skill in the art to which the disclosed subject matter belongs. Although methods and materials similar or equivalent to those described herein can be used in its practice, suitable methods and materials are described below.

The term "neurodevelopmental disorder" refers to any condition, disease, or disorder characterized by abnormal neurodevelopment and/or basic biobehavioral processes, including attentional and perceptual processing, executive function, inhibitory control (e.g., sensory gating), social cognition, and communication and affiliative behaviors. Exemplified neurodevelopmental disorders include attention deficit hyperactivity disorder, schizophrenia, obsessive-compulsive disorder, mental retardation, and autistic spectrum disorders. Some neurodevelopmental disorders can be at least in part caused by antibody-mediated or autoantibody-mediated damage to neural tissue, including for example, autistic spectrum disorders, opsoclonus-myoclonus syndrome, obsessive-compulsive disorder (OCD) and tics, cerebral palsy, mental retardation, seizures, articulation disorder, learning disabilities (i.e., reading or arithmetic), verbal or performance aptitude deficits, and attention deficit disorder. Further information on neurodevelopmental disorders can be found, for example, through the Neurodevelopmental Disorders Branch of the National Institute of Mental Health (worldwide website address at nihm.nih.gov/dptr/b2-nd.cfm).

The term "autism spectrum disorder" or "autistic spectrum disorder" interchangeably refer to a spectrum of neurodevelopmental disorders characterized by impaired social interaction and communication accompanied by repetitive and stereotyped behavior. Autism includes a spectrum of impaired social interaction and communication, however, the disorder can be roughly categorized into "high functioning autism" or "low functioning autism," depending on the extent of social interaction and communication impairment. Individuals diagnosed with "high functioning autism" have minimal but identifiable social interaction and communication impairments (i.e., Asperger's syndrome).

As used herein, the term "subject" or "patient" refers to normal (control) individuals or to test individuals who are being or who have been tested for autism.

As used herein, the term "treat" is used herein to mean to relieve or alleviate at least one symptom of a disease in a subject. Within the meaning of the disclosed subject matter, the term "treat" also denotes to arrest, delay the onset (i.e., the period prior to clinical manifestation of a disease) and/or reduce the risk of developing or worsening a disease.

It is to be noted that the term "a" entity or "an" entity refers to one or more of that entity. For example, a protein refers to one or more proteins or at least one protein. As such, the terms "a", "an", "one or more", and "at least one" can be used interchangeably herein. The terms "comprising," "including," and "having" can also be used interchangeably. In addition, the terms "amount" and "level" are also interchangeable and can be used to describe a concentration or a specific quantity. Furthermore, the term "selected from the group consisting of" refers to one or more members of the group in the list that follows, including mixtures (i.e. combinations) of two or more members.

The term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to +/−20%, up to +/−10%, up to +/−5%, and still up to +/−1% of a given value. Alternatively, particularly with respect to biological systems or processes, the term can mean within an order of magnitude, within 5-fold, and more particularly within 2-fold, of a value. With reference to pharmaceutical compositions, the term "about" refers to a range that is acceptable for quality control standards of a product approved by regulatory authorities.

Functional MRI

Changes in neuronal activity can be accompanied by specific changes in hemodynamic functions such as cerebral blood flow, cerebral blood volume, and blood oxygenation. Functional magnetic resonance imaging (fMRI) has been used to detect these physiologically induced changes in response to visual and auditory stimulation, somatosensory activation, motor tasks, and cognitive activity. During cognitive activity, the blood flow into the active region of the brain increases considerably compared with the tissue oxygen uptake which results in an increase in blood oxy-hemoglobin content. The susceptibility difference between diamagnetic oxy-hemoglobin and paramagnetic deoxy-hemoglobin creates local magnetic field distortions that cause a dispersion in the processional frequency of the water protons and a concomitant change in the magnetic resonance (MR) signal intensity which is proportional to the ratio of oxyhemoglobin to deoxyhemoglobin. These signal-intensity alterations related to blood oxygenation are termed the BOLD (blood oxygenation-level-dependent) effect. The voxels in which paramagnetic hemoglobic content is decreased are detected and colored in an fMRI image. These colors indicated the presence of neural activity that is task-related.

A typical fMRI session involves: (a) stimulating a subject (e.g., by asking the subject to perform a periodic task, for example, a task targeting a particular brain region, or be subjected to periodic visual, audio, and/or tactile stimuli); (b) MR imaging a region of the brain supposed to be involved in the accomplishment of that task; and (c) analyzing a time series of acquired images to determine physiological changes in the brain region. Any MRI scanner equipped for fMRI can be used to obtain the images, including but not limited to a 1.5 T GE Twin Speed magnetic imaging scanner. Field strengths vary from 1.5T to 3.0T, however other clinically usable field strengths can also be suitable.

In the presently disclosed subject matter, fMRI images can be acquired using an echo planar T2* weighted gradient echo sequence (e.g., TE=51 ms, TR=3 s, flip angle=83 deg) on an MRI scanner. Contiguous axial slices covering the full brain can be acquired along the Anterior-Posterior Commissure (AC-PC) plane. The number of slices acquired can range from about 10 to about 150 slices or more. In a particular embodiment, about 20 to about 40 slices are acquired. In a particular embodiment, about 27 slices are acquired.

The slices can be acquired with a target field of view (FOV) imaged on a corresponding grid yielding an in-plane resolution and desired slice thickness (mm). High-resolution structural images can be acquired using a 3D SPGR sequence (e.g., 124 slices, 256×256, FOV=220 mm), with a total scan time of about 20 minutes. The total scan time can range from about 2 minutes to about 40 minutes, alternatively from about 15 minutes to about 35 minutes, depending upon the parameters selected. All of these variables (e.g., FOV, grid size, resolution, slice thickness, time) can be modified by imaging specialists to optimize time, resolution, sensitivity and other relevant factors.

Generally, a subject's brain is mapped using functional MRI during a mental exercise performed by the subject to determine areas of local activity in the brain. In the presently disclosed subject matter, the fMRI images can be obtained with specific fMRI auditory stimuli and conducted with alternating time periods of audio clips and silence (see FIG. 10). Each fMRI stimuli can range from about 3 seconds to about 60 seconds of audio clips followed by the same length of time of silence or alternatively with a different time period of silence. The lengths of the epochs can be varied by knowledgeable imaging specialists depending upon specific objectives. The run can include multiple cycles typically ranging from 2 to 10 cycles. In certain embodiments, the run is repeated for 2 to 6 cycles, or alternatively for 4 cycles.

Figure 10:
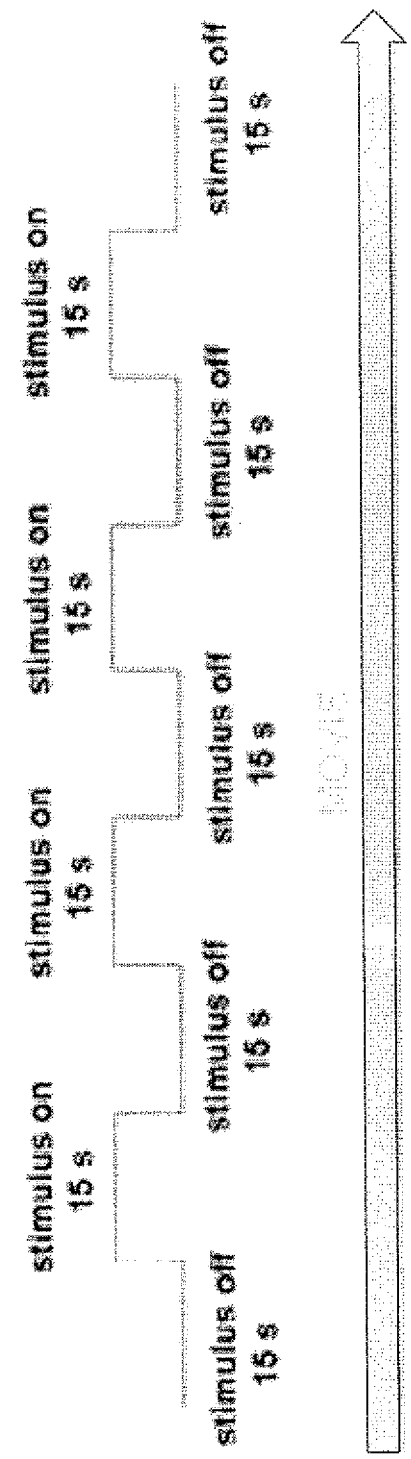
FIG. 10 illustrates an exemplary timeline of alternating time periods of audio clips and silence. The box represents a condition of continuous video for patients who are not sedated which is an adaptation to prevent head motion for non-sedated children.

In a specific embodiment, the fMRI run consists of about 15 second audio clips alternating with about 15 second of silence. The run include multiple cycles and last from about 1 minute to about 4 minutes. In a particular embodiment, the fMRI stimuli can last for about 2 minutes and 30 seconds in duration, followed by a 24-second period of silence. This sequence can be followed by four presentations of 15 seconds audio and silence epochs (FIG. 10).

During the fMRI, different forms of audio stimuli can be used. These stimuli include but are not limited to speech, reverse speech, instrumental music, song, and the same song without lyrics. One or more stimuli can be used during the fMRI. In certain embodiments, one or more of the types of audio stimuli can be presented at least twice. The order of presentation of the stimuli can be patterned or can be randomized across subjects. Stimuli can be pre-recorded and presented passively to subjects via MR-safe headphones.

For the speech stimuli, recordings can be made by familial members or other persons familiar to the subject or patient. For example, and not by way of limitation, parents can be instructed to make a recording where they are talking to their child in a natural and conversational manner. The content of the recordings can be individualized for each subject, and all recording individuals can be instructed to talk about similar topics: recent or upcoming events (i.e., school starting, sports games, trips to the park, beach, or visiting relatives), their favorite foods or activities, and immediate plans after the scan (getting lunch, going to the park, etc.), and the like.

Music stimuli can be excerpts from instrumental or individually-favored songs. In certain embodiments, subjects choose different songs to ensure that the stimulus is familiar and preferred for the individual. In particular, since autistic children often have fixed interests, and can be particularly receptive to familiar stimuli, it can be necessary to select a song that is equally as familiar across all individuals.

Sound stimuli can be power-normalized across voice, music, and song runs using various known programs capable of such stimuli. In certain embodiments, Adobe Audition 1.0 software is used. The use of software ensures that differences in brain activation observed across stimulus type have similar or normalized acoustic properties.

Various obstacles to providing the autistic population with the advantages of functional imaging to map language areas and evaluate language-sensitive systems have prevented large-scale investigations and diagnostic techniques. These obstacles include lack of task compliance in a scanner environment, intolerance to scanner noise, and inability to maintain a stable head position during imaging of awake patients. Previously, functional maps on sedated patients were not considered because of the need for volitional, task-related compliance. Each of these alone is a sufficient contraindication for an imaging study. However, it has been discovered that functional language maps could be reliably acquired on pre-verbal infants while sedated for purposes of neurosurgical planning (Souweidane, et al, Pediatric Neurosurgery 1999, 30:86-9).

Figure 2A:
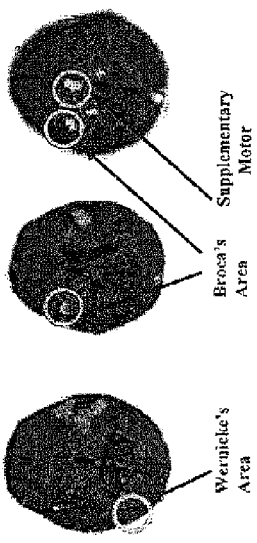
FIGS. 2a and 2b illustrate language mapping of an infant and testing parameters.
Figure 2B:
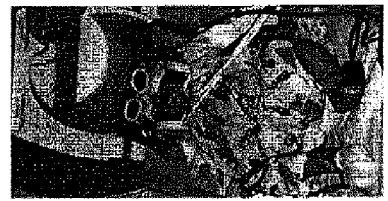
Figure 4A:
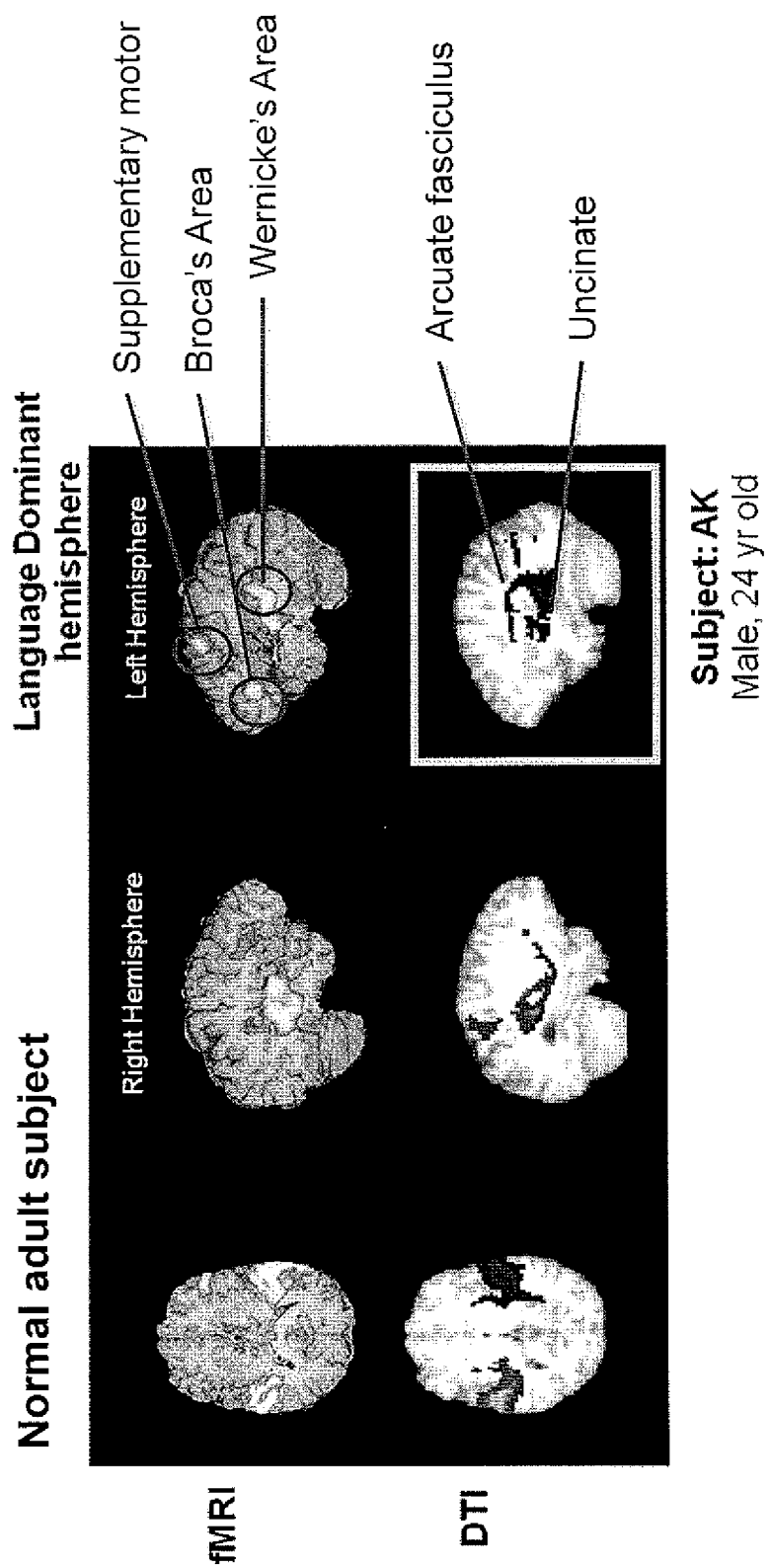
FIGS. 4a through 4e show functional (top row) and DTI (bottom row) images on non-sedated adults showing the expected language regions (fMRI, top right) and the arcuate and uncinate fasciculus (DTI, bottom right) connecting the posterior and frontal language areas of the dominant hemisphere. The top row of each of the figures shows the fMRI of the language maps for each of the subjects (FIGS. 4a-4e), while the bottom row of each figure shows the DTI images that are "seeded" by the functional maps. In each figure, the images on the left are axial (horizontal) views of the brain. The middle images are the sagittal (side) view of the right hemisphere, and the right images are sagittal view of the left hemisphere.
Figure 4B:
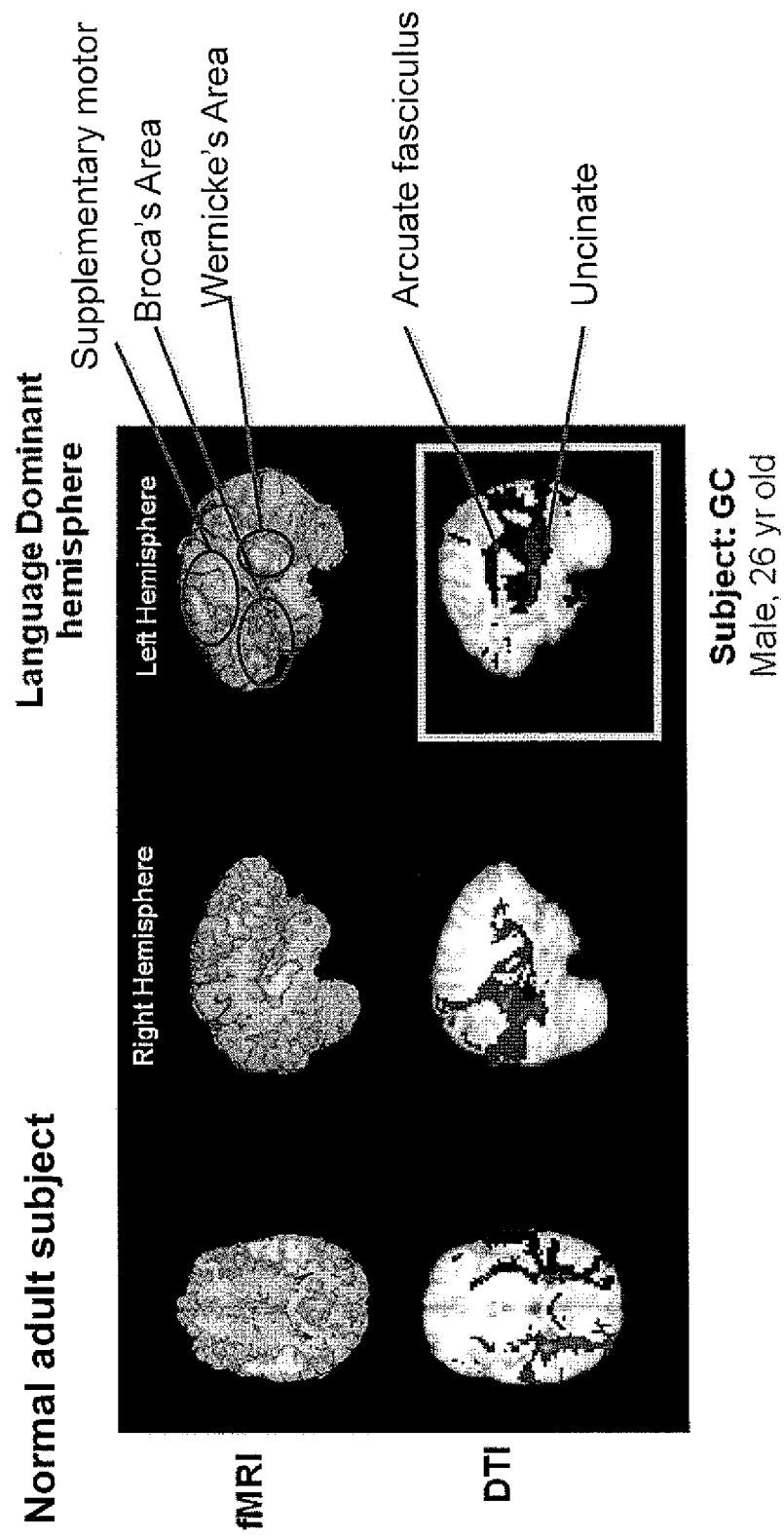
Figure 4C:
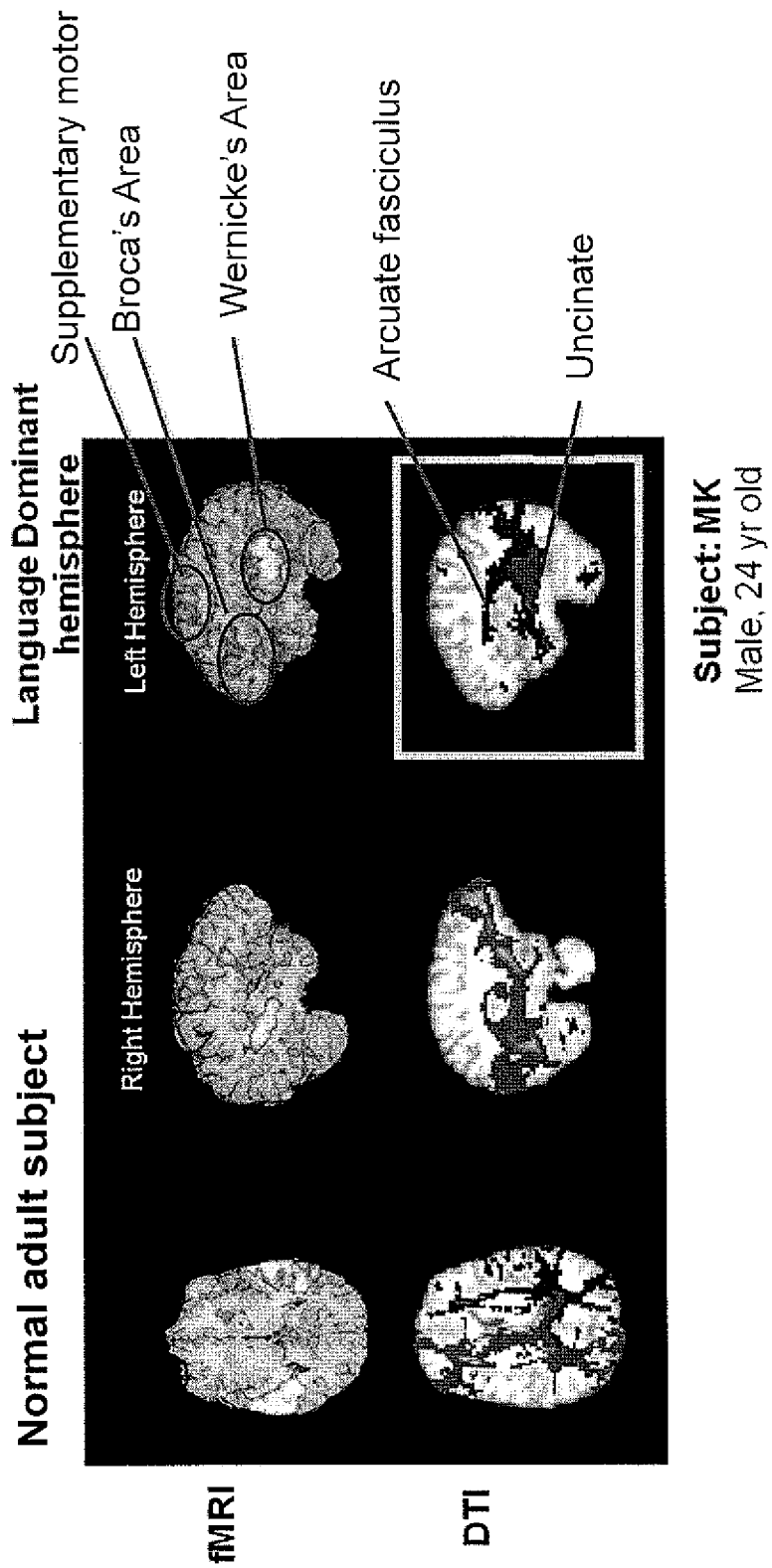
Figure 4D:
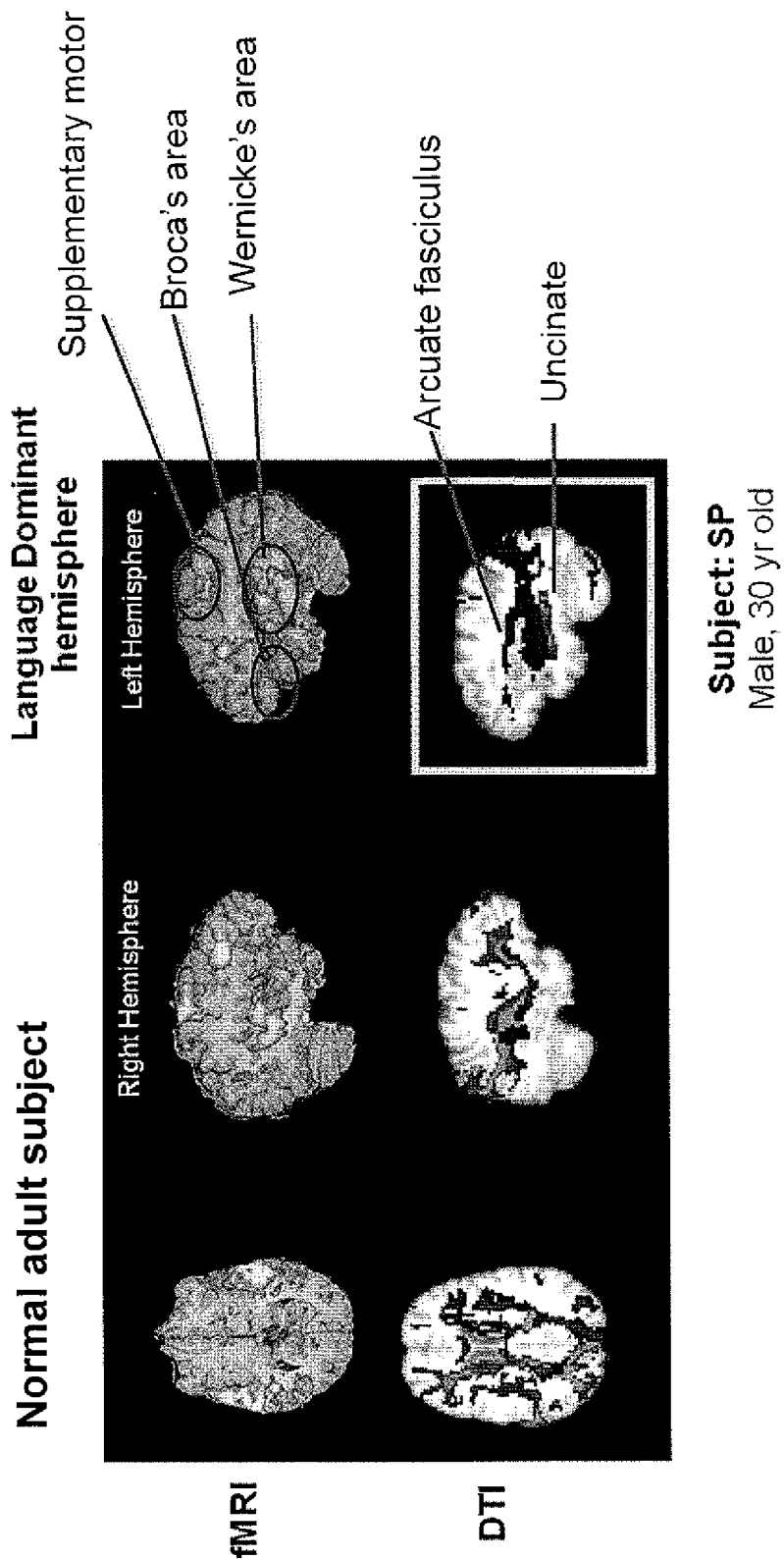
Figure 4E:
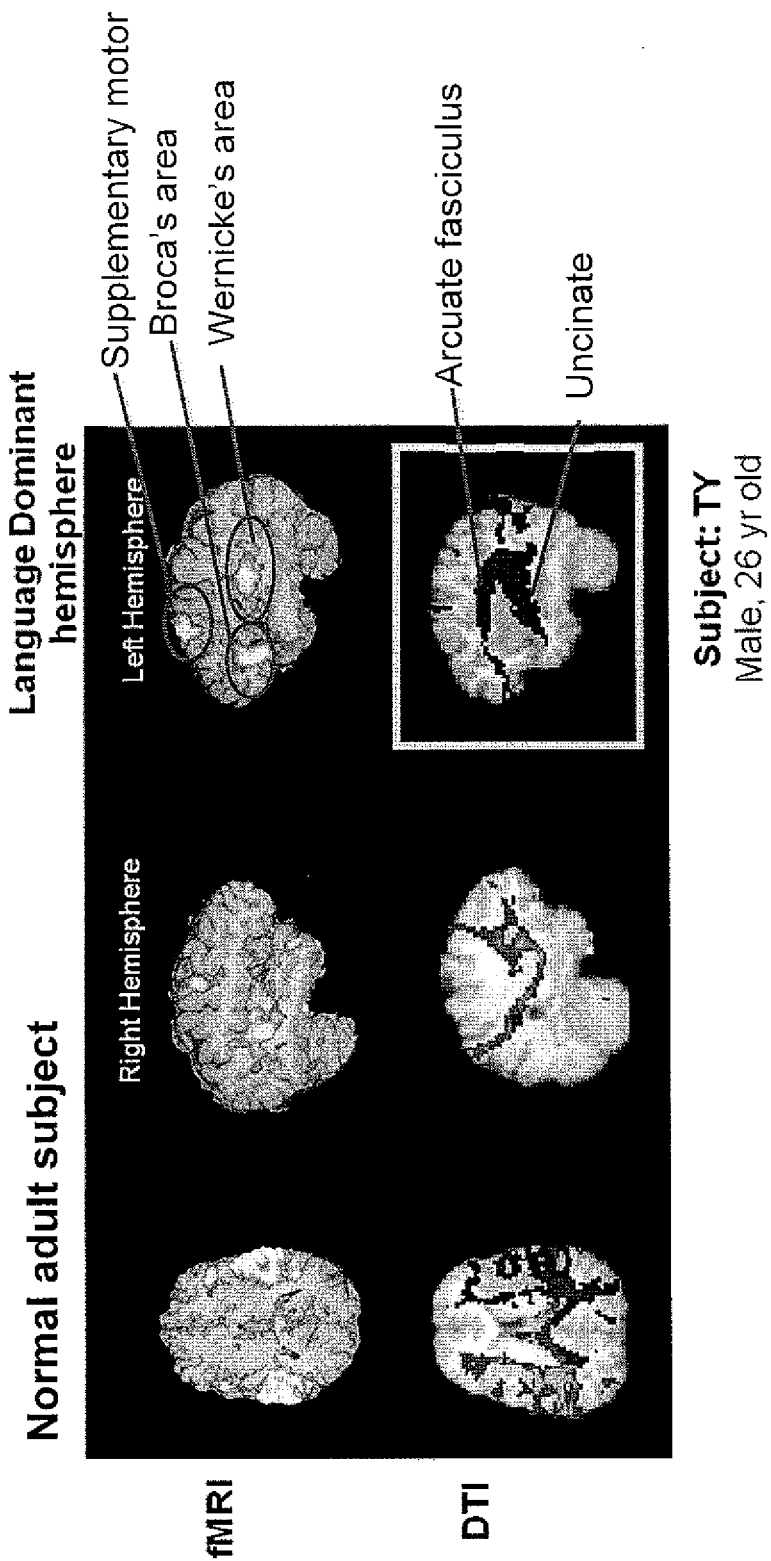
Figure 6A:
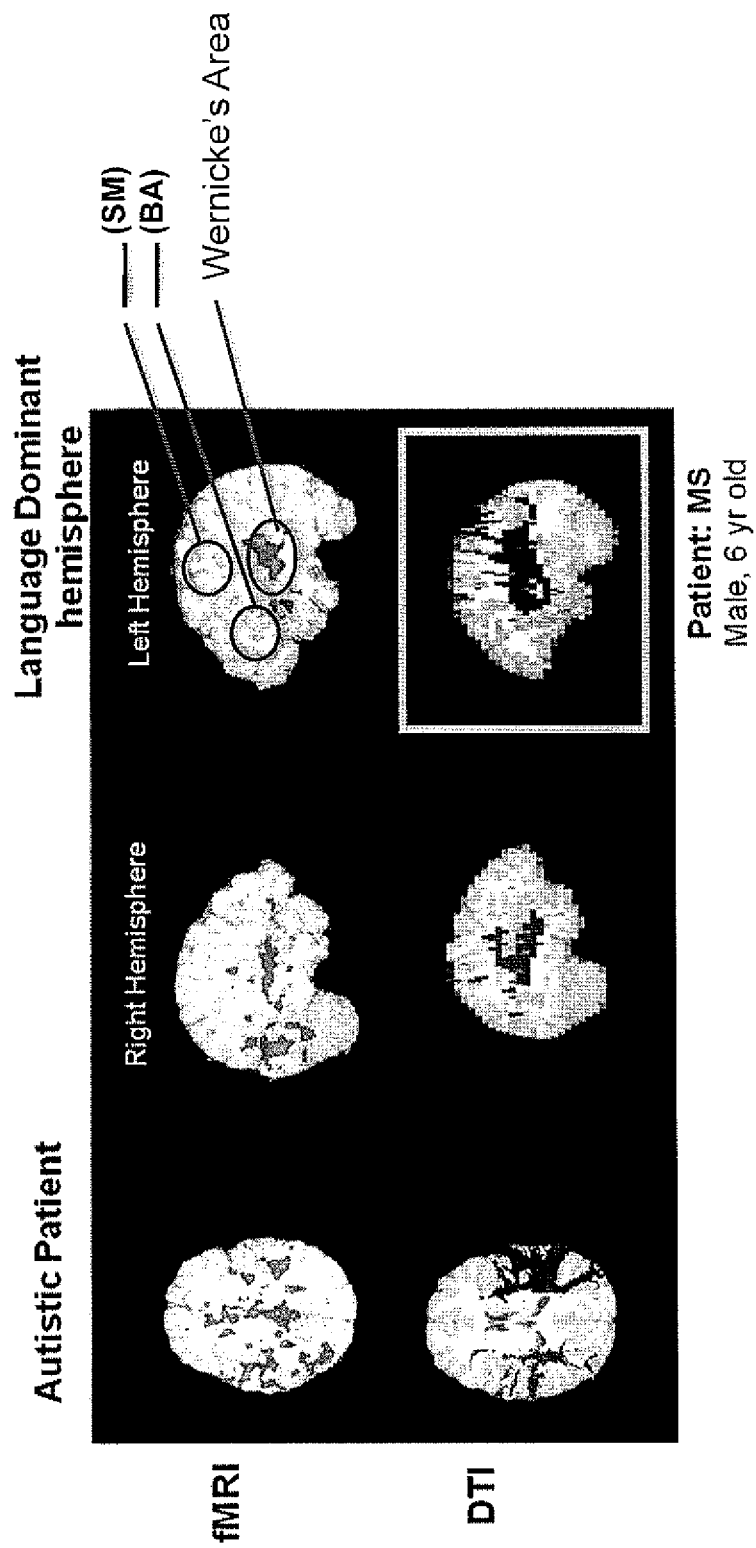
FIGS. 6a through 6e show individual maps of conventionally diagnosed autistic patients sedated for imaging and passive auditory stimulation by recorded narratives of parents. The top row of each of the figures shows the fMRI imaging of the subjects, while the bottom row of each figure shows the DTI images that are "seeded" by the functional maps. In each of FIGS. 6a through 6e, the images on the left are axial (horizontal) views of the brain. The middle images are the sagittal (side) view of the right hemisphere, and the right images are sagittal view of the left hemisphere. Circles indicate the expected areas for language sensitive areas (Broca's and Wernicke's Areas and the Supplementary Motor Area) and the (–) indicates the absence of activity.
Figure 6B:
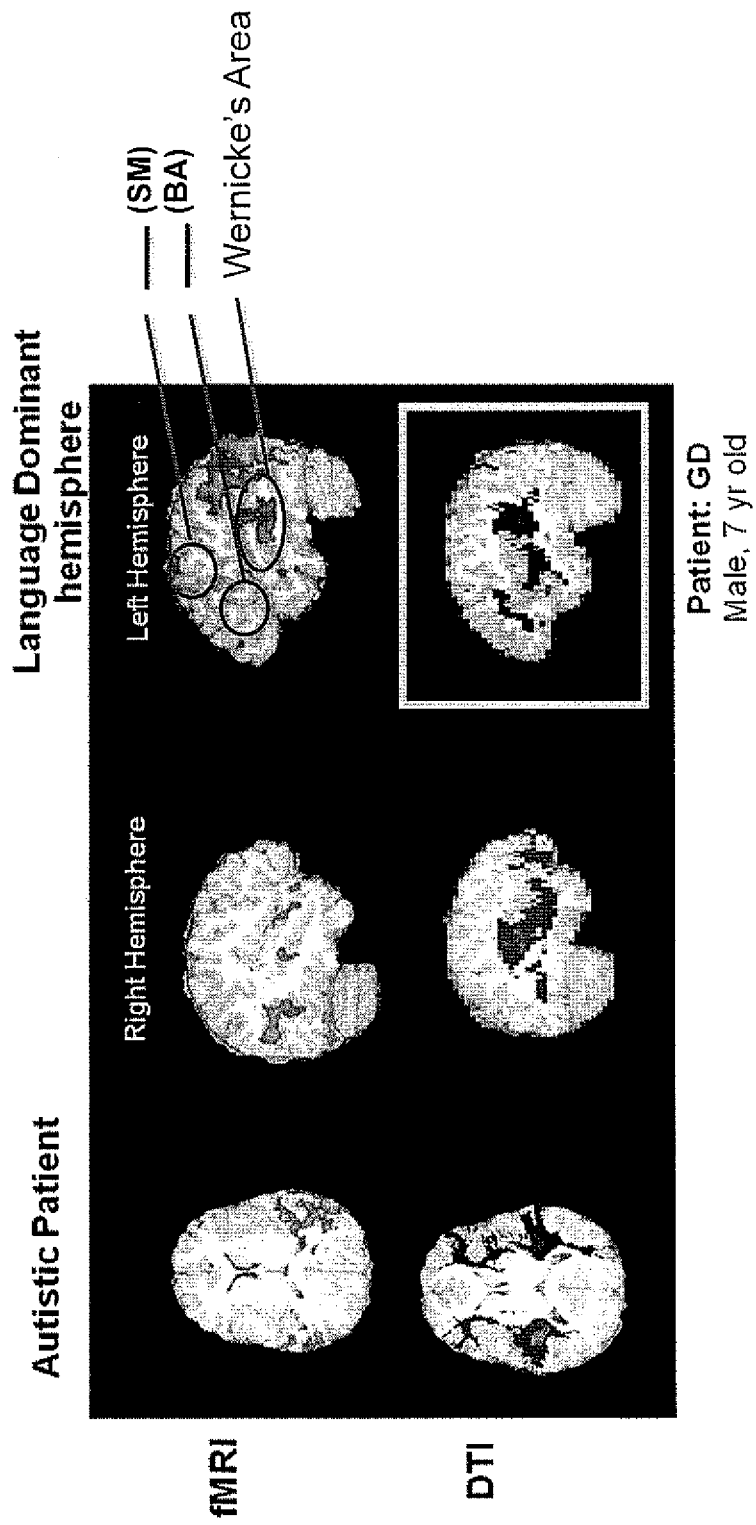
Figure 6C:
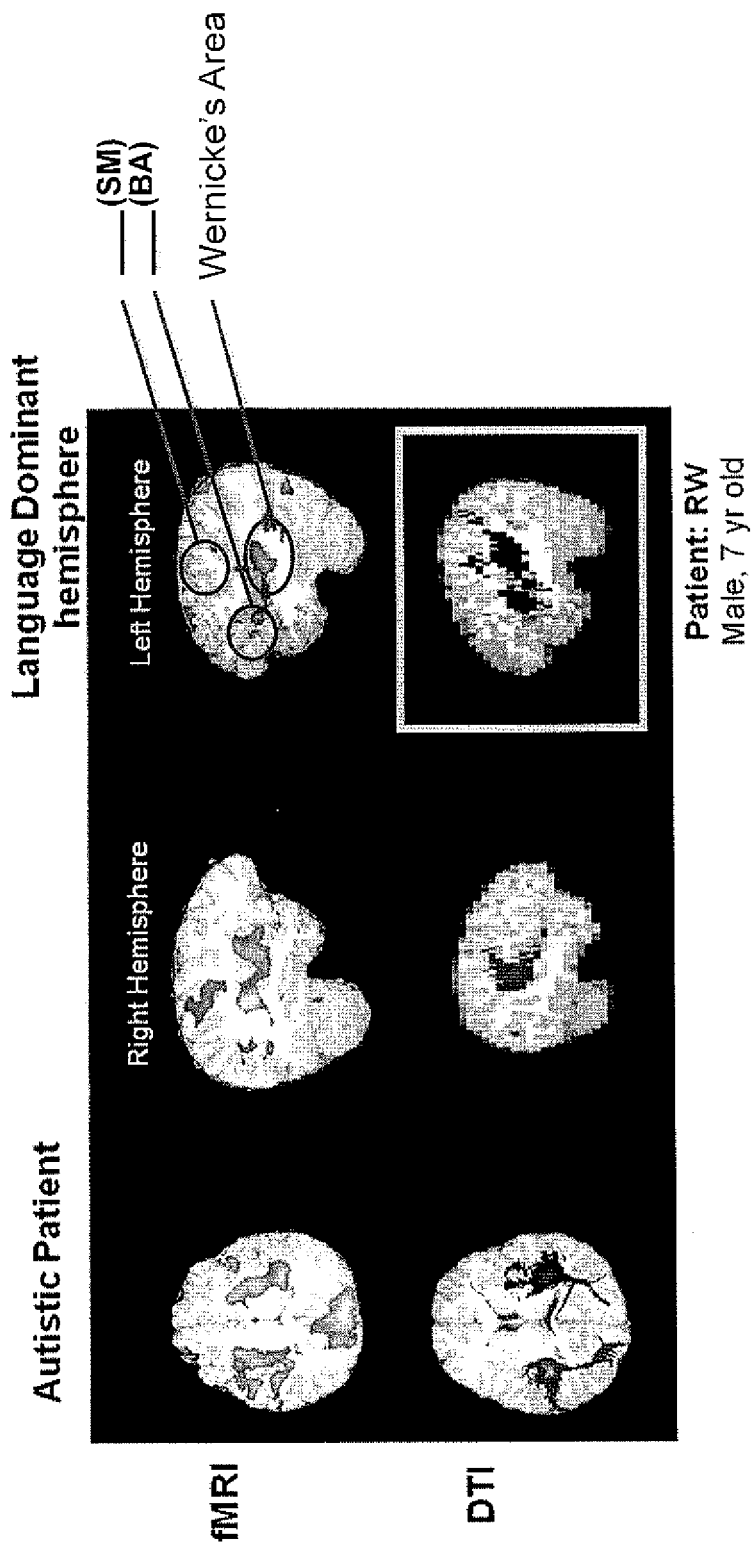
Figure 6D:
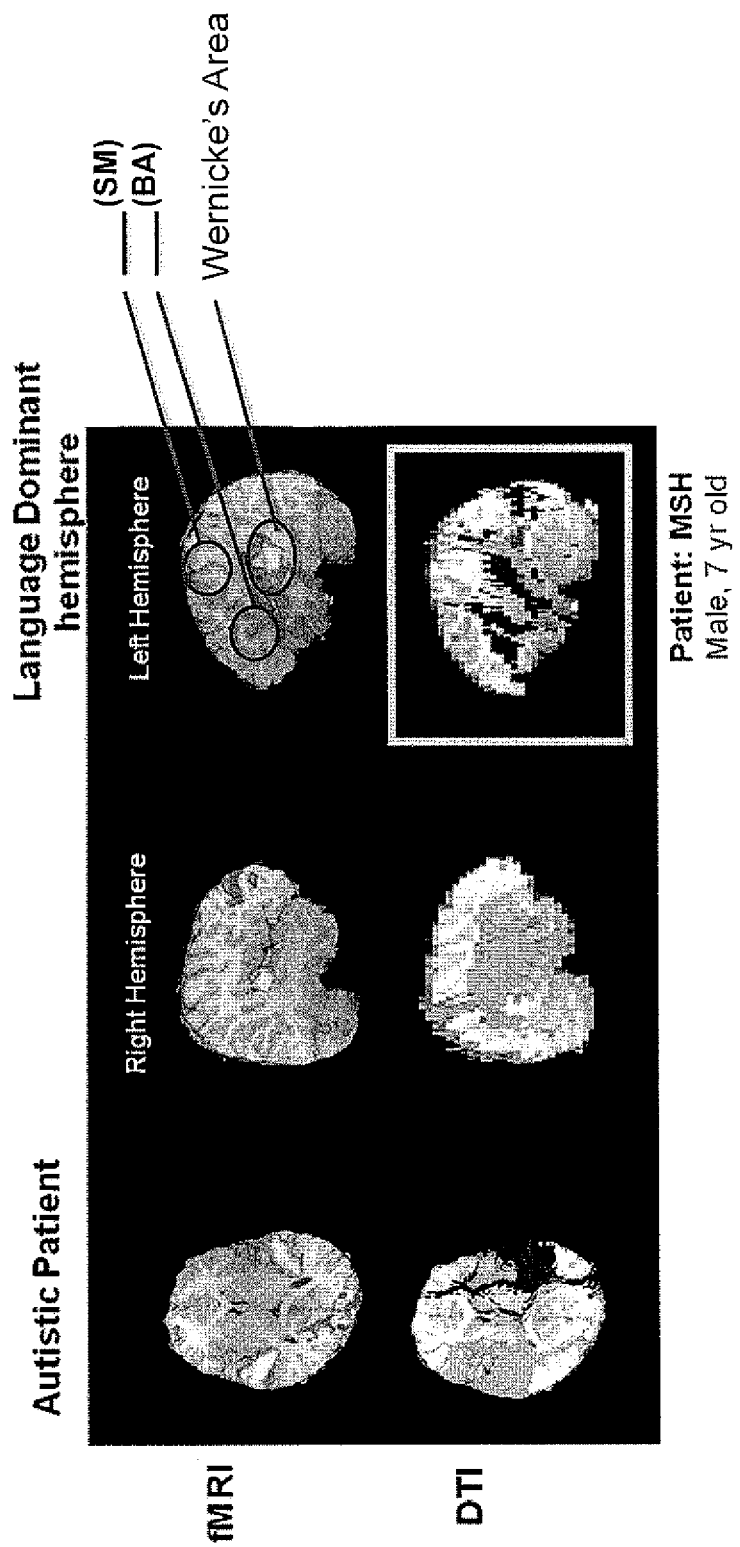
Figure 6E:
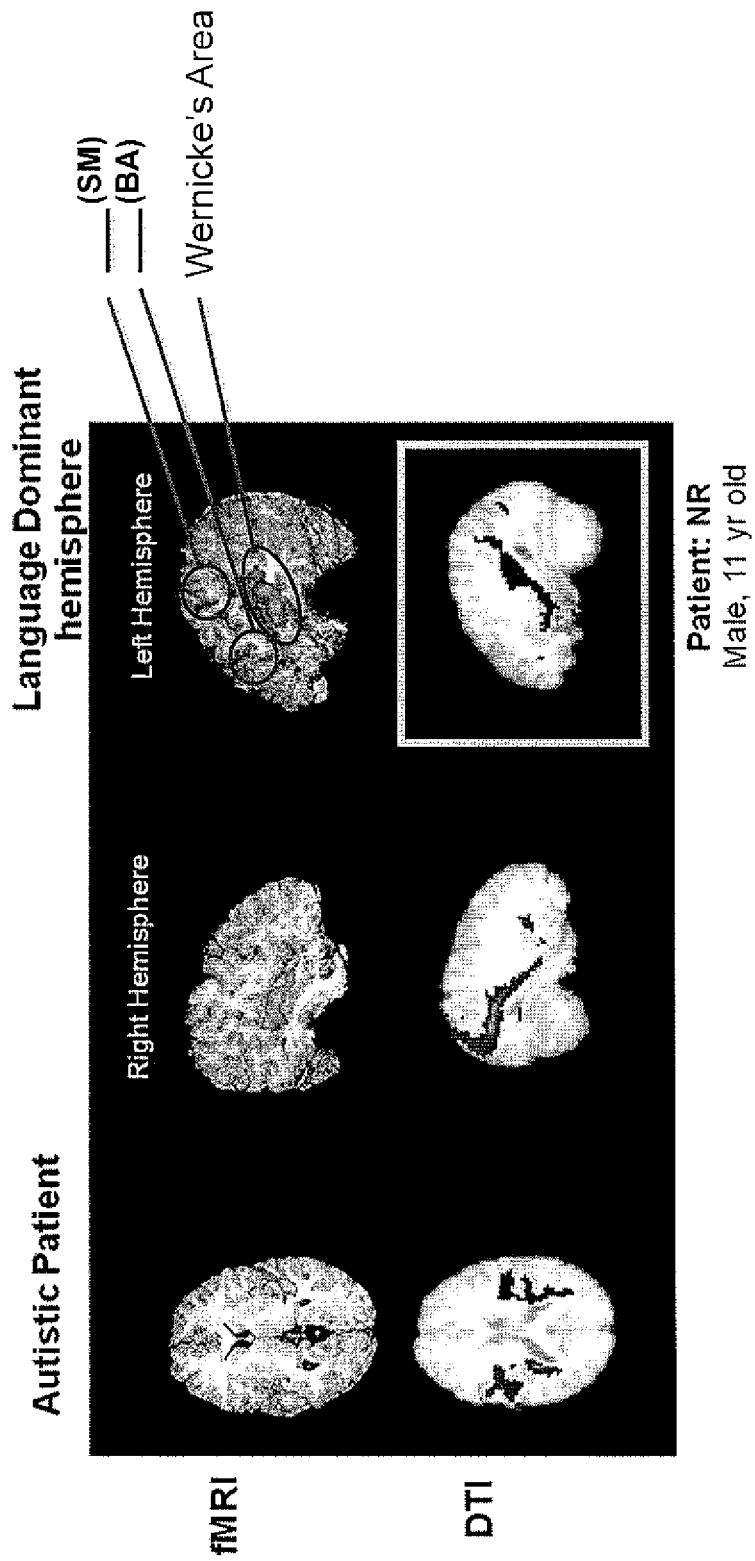

In certain embodiments of the disclosed subject matter, the subjects can be sedated. During sedation, the subjects can be subjected to passive stimulation through listening to recordings of their mothers and/or fathers talking to them. It has been discovered that this passive stimulation is sufficient to elicit the activity of the developing language system for a fifteen-month old child (see FIGS. 2a and 2b). Post-surgical outcomes confirm the validity of the technique using light sedation induced by an appropriate sedative, including but not limited to propofol. Similar techniques have also been applied for neurosurgical planning of children less than 6 years old (see FIG. 3) to study cognitive states of patients who are minimally conscious and unresponsive (Schiff, et al, Neurology 2005, 64:514-523).

fMRI data can be processed using an appropriate software program known in the art. For example, in certain embodiments, the data can be processed using SPM and/or FSL 4.1 software (www.fmrib.ox.ac.uk/fsl/). In this particular application, fMRI results can be analyzed using the feat tool in FSL. Preprocessing of fMRI data consists of brain-extraction, motion-correction, spatial smoothing (Gaussian kernel, FWHM=5 mm), high-pass filtering (cut-off=60 sec), and prewhitening. Pre-processed images can be normalized to standard MNI space and entered into multiple linear regression analyses. First-level general linear model (GLM) analyses for each individual can be done for each type of stimuli separately to identify main effects of auditory stimulation for each condition. Group (controls and ASD) effects and between-group comparisons (control>ASD and vice versa) can be assessed for each type of stimulus. Non-sedated and sedated ASD patients are analyzed separately. Comparisons between ASD and control groups include non-sedated patients only. All of these techniques can be modified depending upon desired standards, practices and specific objectives.

Diffusion Tensor Imaging

The use of diffusion tensor magnetic resonance imaging (DTI) for imaging anisotropic tissue is well-known. DTI provides a novel way to characterize tissues based on sensitivity to microscopic molecular motion of water. Clinical implementation requires strong, fast hardware and careful post processing of diffusion parameters. Diffusion weighted images and derivatives such as three principal diffusivities of the diffusion tensor can be quite specific in reflecting the physical properties of diffusion.

Diffusion weighted imaging (DWI) consists of estimating the effective scalar diffusivity of water, D, in each voxel from a set of diffusion weighted images. During the time of a typical magnetic resonance data acquisition, water molecules diffuse on the order of a few microns, which is comparable to the dimensions of cellular structures, but significantly less than the dimensions of a voxel. Since D is sensitive to the physical properties, composition and spatial distribution of the tissue constituents, the measurement is sensitive to the tissue microstructure and physiological state. Diffusion along a given axis is typically measured by placing a pair of diffusion sensitizing gradient pulses in the same axis in the magnetic resonance (MR) pulse sequence. The gradient pulses impose position-dependent phases on water protons that can be equal in magnitude but opposite in sign and therefore cancel for stationary spins. However, for protons that move between the two gradient pulses, a finite net phase is accumulated. The sum of all phases from all protons results in attenuation of the MR signal due to interference effects. The magnitude of signal attenuation is dependent on the diffusivity of water, and the width, separation and amplitude of the gradient pulses. In a generalized case where the diffusivity can differ in different directions, a diffusion tensor matrix notation is used.

Diffusion Tensor Imaging (DTI) is useful when a tissue has an internal fibrous structure analogous to the anisotropy of crystals. Water will diffuse more rapidly in the direction aligned with the internal structure, and slowly as it moves perpendicular to that direction. The measured rate of diffusion will differ depending on the viewpoint. Therefore, each voxel has one or more parameters: a rate of diffusion and a preferred direction of diffusion. The properties of each voxel of a single DTI image is usually calculated by vector or tensor math from multiple different diffusion weighted acquisitions, each obtained with a different orientation. The directional information can select and follow neural tracts through the brain—a process called tractography.

Any MRI scanner can acquire DTI images, including but not limited to a 1.5 T GE Twin Speed magnetic imaging scanner. DTI images can be acquired on the same scanner using, for example, an 8 channel sense head coil with a single-shot sequence of 55 unique diffusion directions at a b-value=900 with TE=7.8 ms and TR=1700 ms. A single volume (b-value=0) can be acquired and used as a reference to correct for eddy currents and head motion. Isotropic (e.g., 2.5 mm$^3$ voxels) diffusion-weighted data can be acquired for all subjects. Array size can be, for example, 128×128 in a FOV of 32×32 mm.

Slices are acquired, ranging from about 20 to about 75 slices or more. In certain embodiments, from about 40 to about 60 slices are acquired. In a particular embodiment, about 58 slices can be acquired. The total scan time can range from about 2 minutes to about 40 minutes, alternatively from about 15 minutes to about 35 minutes, depending upon the parameters selected. All variables are modifiable by imaging specialists familiar with these techniques in order to enhance particular desired factors such as time, sensitivity, resolution, and post-processing.

DTI data is processed using an appropriate software program known in the art. For example, in certain embodiments, the data is processed using FSL 4.1 software (www.fmrib.ox-.ac.uk/fsl/). Preprocessing of DTI data consists of correction for eddy current and head motion using affine registration and brain extracted to exclude non-brain tissue. Diffusion tensors can be then fitted using dtifit or other specialized software to generate the fractional anisotropy (FA) values for each voxel. Estimation of the distribution of diffusion parameters to model crossing fibers was run using bedpostx for use in tractography analyses. These processing techniques are known to the art and can be modified for specific enhancements and hardware platforms applicable to the presently disclosed subject matter.

DTI tractography can be performed for each individual to isolate tracts within the language network using specified software available for this purpose, including for example, probtractx. Starting from voxels within a specified seed mask, pathways can be tracked using the modified Euler streamlining which draws up to 5,000 streamline samples through estimated probability distributions of diffusion direction from each voxel with a minimum fractional anisotropy (FA) value of about 0.2. The output can be an image, where each voxel contains a value that represents the number of streamline samples from a seed voxel that passes through that particular voxel. In one embodiment, all voxels can be considered with a value greater than 0. Distance correction can be used to correct for the fact that connectivity distribution decreases with distance from the seed mask. See Behrens, et al., NeuroImage, vol. 34, no. 1, pp. 144-155 (2007) for detailed methods of tractography algorithms.

"Seeding" refers to a technique that computationally registers the whole-brain images acquired by fMRI and DTI, and then selects fibers from a "seeded" origin which is defined (in this case) as the region within Herschel's gyrus that is activated by the spoken language. Thus, the "seed" is a region defined both structurally (Herschel's Gyrus) and functionally (active during spoken language stimulation), and is, therefore, comparable across all subjects in spite of expected variations in individual subjects. The size of the region is approximately 1.0 cm in diameter although this can vary. The "target" is a selected region that represents a putative fiber tract, and is identified to determine if two regions of the brain (seed and target) are structurally connected. In this case, the "seed" is considered "Wernicke's Area" and the target is "Broca's Area" and is defined structurally as a 1 cm diameter region of the pars opercularis and functionally as the activity observed within that region during the auditory stimulation. The figures show the "seed" Wernicke's Area and "target" Broca's area for the fiber tracts labeled arcuate and uncinate.

Since tractography results can differ depending on the size and location of the "seed" (origin of the fiber tract) and "waypoint" (target or destination of the fiber tract) masks used, anatomical masks can be created in normal space using the Harvard-Oxford atlas probability distributions, which can be included in software packages. A mask is the area identified as the destination or origin of the nerve fiber tracts identified by DTI. These maps can be transformed into individual DTI spaces to ensure the most systematic creation of individual masks. Voxels with probability values of over about 20% can be included. After transformation into DTI space, the Herschel's mask can be multiplied by the binarized grey-matter skeleton for a specific subject (generated by FLIRT segmentation) to exclude overlapping white matter. This can be done to track fiber projections originating from a specific cortical region and seeding from a major white-matter track can lead to tractography of all projections from that track. Standard masks can be used for Herschel's gyrus which encompasses primary and secondary auditory cortices and inferior frontal gyrus (IFG) pars opercularis (Broca's area).

Because there is a possibility that projections from auditory cortices (Herschel's gyrus) can differ between ASD and control groups, tractography analysis can be conducted to identify all tracts originating from primary auditory cortex before specifying waypoint masks to isolate specific tracts. Inspection of projections from individual subjects confirms that both patients and controls show the expected dorsal and ventral white matter projections. Appropriate waypoint masks can be specified to isolate dorsal and ventral tracts separately. Waypoint masks can be chosen based on known anatomy, and can be confirmed by visual inspection to assure that they overlapped the activity engaged during the auditory stimulation all tracts originating from the Herschel's gyrus seed. All steps can be varied as needed by skilled image processors depending upon specific goals, formats, platforms, software versions, scanner vendors, and other site-specific factors.

Application of Imaging to Autism

The presently disclosed subject matter indicates that ASD results from atypical neural circuitry that mediates language functions. Specifically, whereas a typical language network elicited by object naming and passive listening tasks involves Broca's Area (left inferior frontal gyrus), Wernicke's Area (left superior temporal gyrus) (STG) and the supplementary motor area (left medial frontal gyms) (as illustrated in FIG. 1), it has been found that the language network of an individual with autism spectrum disorder engages an alternative constellation of regions.

The disclosed subject matter provides an early and objective indicator of autism by imaging the brain to obtain an "autism pattern", which is determined by fMRI response patterns and correlated with DTI. Either or both results can be indicative of risk for autism. The fMRI response pattern to auditory language stimulation shows sparse functional representation in the frontal lobe and STG (left and right hemispheres), but not the primary auditory cortex. The DTI response pattern is based on the Wernicke's Area or primary auditory cortex (A1) to Broca's Area connectivity indicating the absence of, or compromised integrity of connectivity between temporal and frontal language areas on a dominant (left) hemisphere.

The "autism pattern" is based on approved and commercially available imaging sequences: EPI (Echo-planar imaging) and DTI require a total of about 20 minutes to about 40 minutes of imaging time. Echo planar images can be used to acquire functional data, but other fast sequences tuned to variations in blood oxygen-levels can be applied. The test can be performed under light sedation and at an age when autism is first suspected, usually as early as about 2-3 years of age. The test can also be performed without sedation in children able to maintain a stable head position for the duration of the tests.

The autism pattern provides a physiological diagnostic for autism and an objective indicator of therapeutic progress. There are no toxicity concerns for MR imaging without contrast because of the absence of radiation, and therefore no contraindications for multiple tests. A reservation to multiple tests can be based on the need for sedation and is determined individually for each patient.

EXAMPLES

The disclosed subject matter will be better understood with reference to the following Examples, which are provided as exemplary of the disclosed subject matter, and not by way of limitation.

Example 1

Functional Mapping of Normal and Autistic Subjects

Thirty-eight autistic children were scanned either with (n=27) or without (n=11) sedation. When sedation was used, the scans were acquired for medical purposes and consent was obtained from both parents to use their child's clinical scans in the research protocol. Although it is generally thought that sedation can result in differences in the amplitude of fMRI activation, it is medically indicated to rule out organic disease in young children with delayed development and have been used routinely for neurosurgical planning purposes (Hirsch et al., Neurosurgery 2000, 47(3):711-722). Data from children who would not be able to tolerate these MRI scans otherwise are most important to isolate early biological signs of the disease and to characterize brain abnormalities in the lowest-functioning individuals.

18 Awake and healthy controls were run at the Columbia fMRI Center Program for Imaging and Cognitive Sciences (PICS). Data from an additional 2 controls, and 1 autistic subject were excluded due to excessive movement. Parents were asked to provide speech recordings, song stimuli, as well as a DVD or TV show for their child to watch during scanning. All children were given the option of going through a practice scan to acclimate to the scanner environment. Functional and structural images for sedated children were collected at Morgan Stanley Children's Hospital Imaging Suite on a 1.5 T GE magnetic imaging scanner.

fMRI stimuli. fMRI runs consisted of 15 sec audio clips alternating with 15 sec of silence. Each run was 2 min and 29 sec in duration and consisted of a 24 sec period of silence followed by 4 presentations of 15 sec audio and silence epochs (FIG. 10). Each of five types of audio stimuli was presented two times: speech, reverse speech, instrumental music, song, and the same song without lyrics. The order of presentation was randomized across subjects. Stimuli were pre-recorded and presented passively to subjects via MR-safe headphones.

For the speech stimuli, parents were instructed to make a recording where they are talking to their child in a natural and conversational manner. Parents started out with assuring their child and reminding him or her to hold still for the scan. The content of the recordings was individualized for each child. Music stimuli were excerpts from instrumental and favorite songs. It was necessary that each child choose their own songs to ensure that the stimulus was familiar and preferred for individual children. Sound stimuli were power-normalized using Adobe Audition 1.0 software.

MRI Acquisition. fMRI images were acquired using an echo planar T2* weighted gradient echo sequence (TE=51 ms, TR=3 s, flip angle=83 deg). Twenty-seven contiguous axial slices covering the full brain were acquired along the AC-PC plane, with a 192×192 mm field of view (FOV) imaged on a 128×128 grid yielding an in-plane resolution of 1.56×1.56 mm and slice thickness of about 4.5 mm. High-resolution structural images were acquired using a 3D SPGR sequence (124 slices, 256×256, FOV=220 mm), with a total scan time of approximately 11 minutes. Diffusion tensor imaging (DTI) images were acquired using a echo-planar sequence (TR=1700 ms, TE=7.8 ms, 55 directions, b=900 s/mm^2). Fifty eight slices were acquired. The FOV was 32×32 mm. The total scan time for the DTI acquisition was approximately 13 minutes.

Data Analysis. DTI and fMRI data were processed using FSL 4.1 software. fMRI results were analyzed using the FSL feat tool. Preprocessing data included brain-extraction, motion-correction, spatial smoothing (Gaussian kernel, FWHM=5 mm), high-pass filtering (cut-off=60 sec), and pre-whitening. The images were then normalized to standard MNI space and entered into multiple linear regression analyses.

First-level general linear model (GLM) analyses for each individual were done for speech, music, song, and reverse runs separately to identify main effects of auditory stimulation for each condition. Group effects and between-group comparisons (control>ASD and vice versa) were assessed for each type of stimulus: speech, music, song, song without lyrics. Analyses for ASD subjects considered non-sedated and sedated patients separately. Comparisons between ASD and control groups included non-sedated patients only.

Preprocessing of DTI data consisted of correction for eddy current and head motion using affine registration and brain extracted to exclude non-brain tissue. Diffusion tensors were then fitted using dtifit to generates FA values for each voxel. Estimation of the distribution of diffusion parameters to model crossing fibers was run using bedpostx for use in tractography analyses.

DTI tractography was performed for each individual to isolate tracts within the language network using probtractx. Starting from voxels within a specified seed mask, pathways are tracked using the modified Euler streamlining which draws up to 5000 streamline samples through estimated probability distributions of diffusion direction from each voxel with a minimum fractional anisotropy (FA) value of 0.2. All voxels with a value greater than 0 were considered. Distance correction was used.

Anatomical masks were created using the Harvard-Oxford atlas probability distributions included in the FSL software package. These maps were transformed into individual DTI spaces. Voxels with probability values of over 20% were included. After transformation into DTI spaces, the Herschel's mask was multiplied by the binarized grey-matter skeleton for that subject.

Tractography analysis was conducted to identify all tracts originating from primary auditory cortex before specifying waypoint masks to isolate specific tracts. Inspection of projections from individual subjects confirm that both patients and controls show the expected dorsal and ventral white matter projections. Appropriate waypoint masks were specified to isolate dorsal and ventral tracts separately. Waypoint masks were chosen based on known anatomy that were also confirmed by visual inspection of all tracts originating from the Herschel's gyrus seed.

Results. FIGS. 3a and b show functional maps of sedated language-normal children during passive "listening" to recorded words. The images show the activity in the posterior (bottom circle) and frontal (top circles) sections on the dominant left hemisphere. These figures confirm that sedated language-normal children age-matched to the autistic population engage expected language-sensitive regions of the brain during passive stimulation of spoken language. They also confirm the ability to perform these maps on individual patients rather than groups. These cases are age-matched to the population of patients targeted by diagnosis of ASD. Both patients received these language maps for the purpose of neurosurgical planning. These procedures are provided as standard of care for both adults and children in order to reduce risk of avoidable morbidity due to surgical procedures. Together, FIGS. 2 and 3 illustrate the language mapping technique for sedated children over a range of ages from 15 months to 6 years.

FIGS. 4a-e show functional and DTI images on non-sedated adults showing the expected language regions and the connection pathways: accurate fasciculus and uncinate (bottom right) connecting the posterior and frontal language areas of the dominant hemisphere (left). These Figures illustrate the characteristics of a healthy language-sensitive network in individual adults.

FIGS. 5a-5c shows the group average language map for age-matched healthy volunteers. The figures document the across-subject generality of the language system as assessed by passive listening using fMRI (top row). Middle and bottom rows illustrate the absence of frontal (Broca's Area) for ASD patients (non-sedated, middle row; sedated, bottom row). FIG. 5 illustrates the hyposensitivity of frontal language areas in autistic patients during stimulation with spoken language relative to age-matched healthy control subjects. There is no evidence that this finding is affected by sedation (FIGS. 5b and 5c).

FIGS. 6a-6e show individual diagnosed autistic patients sedated for imaging and passive auditory stimulation by recorded narratives of parents. As with the figures of "language-typical" subjects, the top row shows the associated DTI seeded at the primary auditory cortex confirmed both by the anatomy and by the functional maps. FIGS. 6a-6e illustrate the absence of, or reduced integrity of, the arculate fasciculus in these subjects consistent with the functional hypoactivity. In each case, the images show hyposensitivity of Broca's Area (BA) evidenced by the failure to activate during auditory language stimulation. The figures also illustrate hypoactivity of the supplementary motor (SM) regions and may also be considered as a diagnostic indicator of autism spectrum disorder.

Figures 7A, 7B:
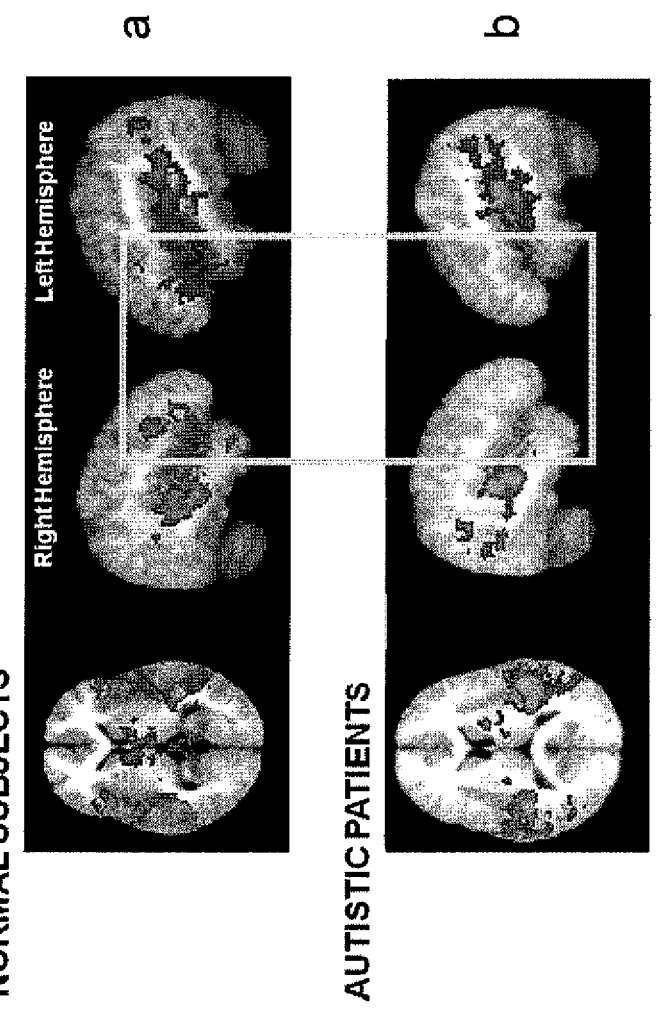
FIGS. 7a and 7b show the average difference between the group fMRI images for normal controls (FIG. 7a) and the sedated and non-sedated autistic patients (FIG. 7b) during passive listening to spoken language. The box highlights the hyposensitivity frontal regions for autistic subjects including Broca's Area, Wernicke's Area and the Supplementary Motor Area.

FIGS. 7a and 7b show the average difference between the group fMRI images for normal controls (FIG. 7a) and the sedated and non-sedated autistic patients (FIG. 7b) during passive listening to spoken language. The Figures show group comparison of language-typical age-matched healthy volunteers (n=18) and autistic patients (n=38). The rectangle illustrates the hypoactivity of frontal lobe activity for autistic subjects. Thus, it is discovered that ASD is characterized by hyposensitivity to spoken language. The images confirm that the frontal language areas are hyposensitive to language stimulation in autistic patients.

Figure 8:
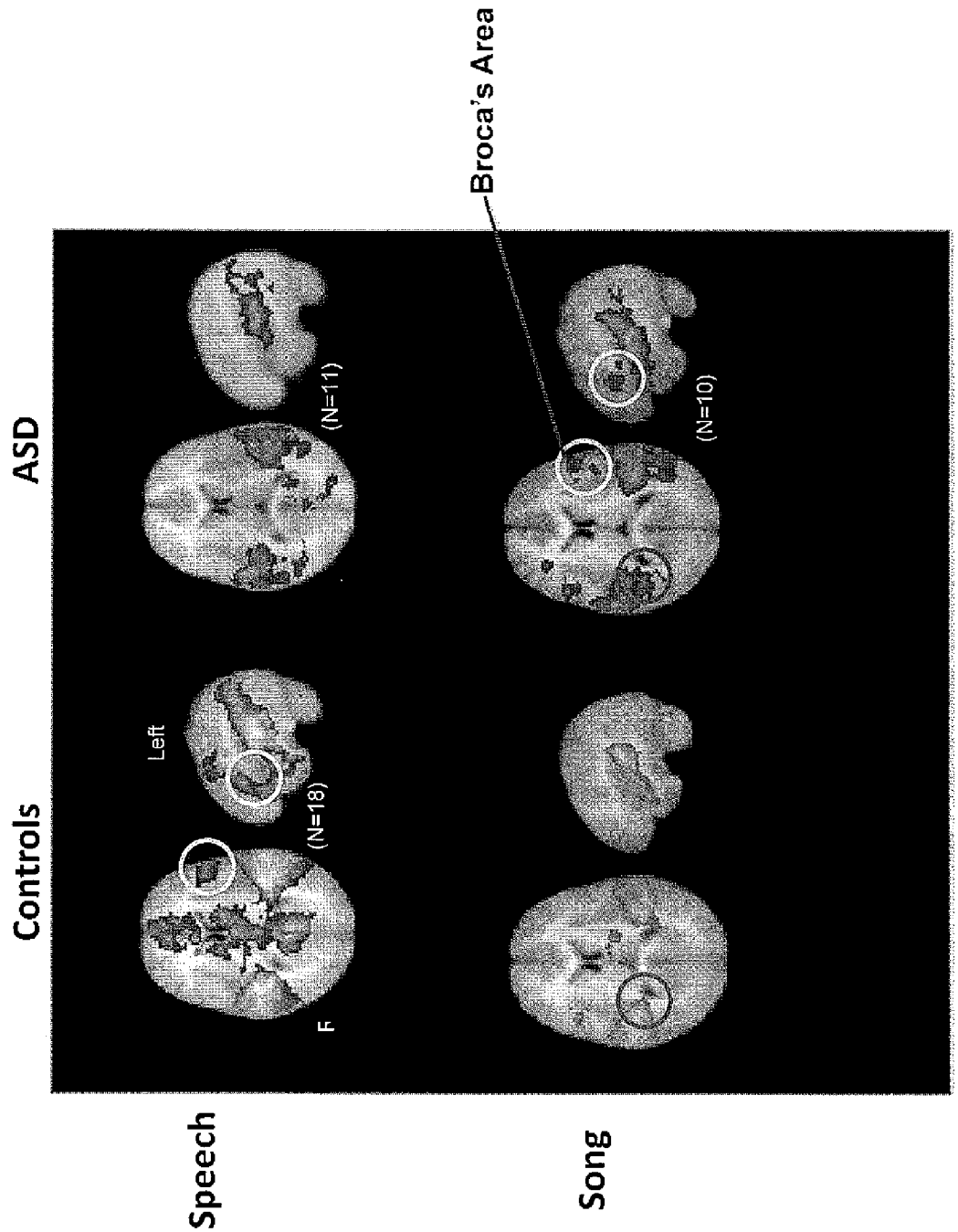
FIG. 8 shows group results for two tasks, listening to recorded speech (top row) and listening to recorded songs with lyrics (bottom row) for age-matched healthy controls (left column) and ASD patients (right column).

FIG. 8 shows group results for two tasks, listening to recorded speech (top row) and listening to recorded songs with lyrics (bottom row) for age-matched healthy controls (left column) and ASD patients (right column). This figure shows the average difference between the group images for normal controls (n=18) and the autistic patients (n=38), confirming the finding observed on each patient that the frontal language areas are hyposensitive to language stimulation in autistic patients (top row) but are responsive to songs with lyrics (bottom row).

Note that the ASD patients activate Broca's Area (circles) during song but not language. Hence, it is discovered that the difference in language maps between spoken language and song may provide an imaging indicator of autism. Autistic subjects activate Broca's Area during stimulation with songs including lyrics, however this is not the case with speech.

Figure 9:
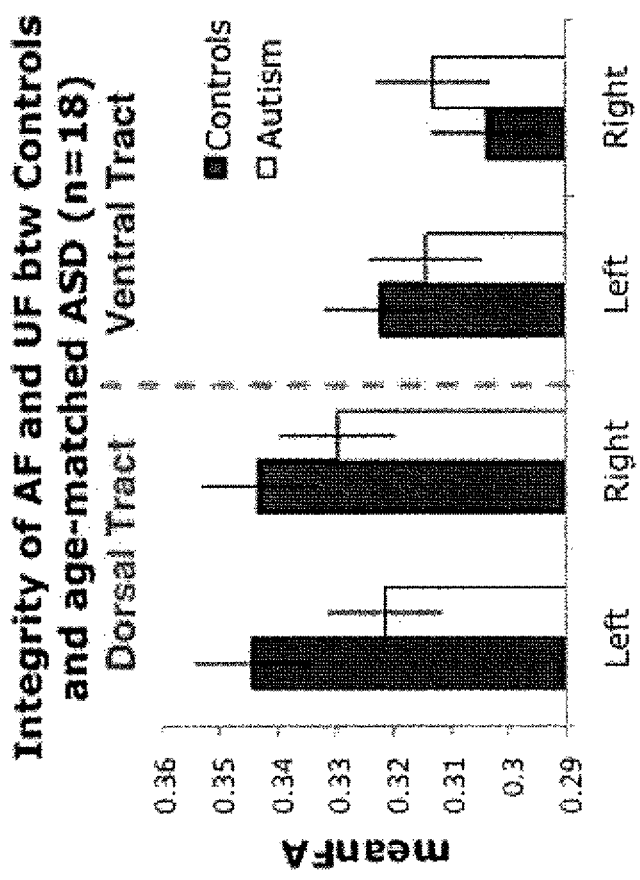
FIG. 9 illustrates the reduced integrity of the arcuate fasciculus for autistic patients relative to age matched healthy controls. The dependent variable is the fractional anisotrophy (FA), an indicator of the connectivity of the nerve fiber tract.

FIG. 9 illustrates the reduced integrity of the arcuate fasciculus based on fractional anisotropy FA, in autistic patients relative to age matched healthy controls. The ventral (uncinate fasciculus) tract is within normal limits. This finding demonstrates a physiological underpinning for the reduced sensitivity of the frontal (Broca's Area) region in ASD.

Example 2

Spread and Amplitude of BOLD Activation within Anatomically Defined Regions of Interest (ROIs) for Primary Auditory Cortex and Superior Temporal Gyrus Subjects: This study is a retrospective analysis of data acquired from 2008-2010 for an independent study designed to investigate the neural mechanisms that underlie language impairment in autistic children. Fifteen non-autistic controls (mean age=12.13, SD=4.34, age range 4.19-17.78), and twelve autistic patients (mean age=12.40 SD=4.70, age range 7.01-22.47) were imaged while alert, and twenty-seven autistic patients (mean age=8.62, SD=3.14, age range 5.41-17.93) received routine clinical MRI evaluations (structural and functional) under propofol sedation. The parents or guardians of all subjects gave permission to include their images in this study in accordance with procedures approved by the Institutional Review Board and HIPAA guidelines. Autistic subjects were recruited by means of physician referral, and control subjects were recruited by posting flyers around the hospital. The control group included five girls (mean age=12.28, SD=5.47, age range 5.05-17.51) and 10 boys (mean age=12.05, SD=4.00, age range 4.19-17.78) while the autistic subjects included two female subjects (mean age=12.02, SD=5.14, age range 8.38-15.63) and 10 male subjects (mean age 12.48, SD 4.90, age range 7.01-22.47). Detailed subject information is provided in Table 1 (A-C). Groups were matched for age and maternal education. Due to excess head movement, two control and four autistic subjects were excluded from the study.

The course of medical treatment was not altered for subjects included in this study. Control subjects were excluded if they were diagnosed with any psychiatric conditions or if they were taking any psychiatric medications. All autistic subjects were evaluated by the referring physician and referred only if they met all inclusion and exclusion criteria.

TABLE 1

Subject Information

| Subject | Init | Dominant Hand | Sex | Age at Scan | ADI-R Scores Social | Lang | Rep Beh | Propofol Level |
|---|---|---|---|---|---|---|---|---|
| A. Controls - Non-Sedated | | | | | | | | |
| 1 | bt | R | M | 13.55 | | | | |
| 2 | cp | R | M | 14.62 | | | | |
| 3 | er | R | M | 17.78 | | | | |
| 4 | et | R | M | 11.1 | | | | |
| 5 | ij | L | M | 16.84 | | | | |
| 6 | jp | R | M | 4.19 | | | | |
| 7 | jr | R | F | 15.93 | | | | |
| 8 | kq | R | F | 15.02 | | | | |
| 9 | la | R | M | 9.87 | | | | |
| 10 | mp | R | F | 5.05 | | | | |
| 11 | nf | R | F | 7.9 | | | | |
| 12 | op | R | M | 13.07 | | | | |
| 13 | rl | R | F | 17.51 | | | | |
| 14 | sf | R | M | 9.64 | | | | |
| 15 | tp | R | M | 9.84 | | | | |
| Mean | | | | 12.13 | | | | |
| Standard Deviation | | | | 4.34 | | | | |
| B. Autism - Non-Sedated | | | | | | | | |
| 1 | mb | R | M | 16.72 | 20 | 17 | 6 | |
| 2 | wm | A | M | 7.01 | 22 | 18 | 6 | |
| 3 | nr | R | M | 10.85 | 22 | 17 | 6 | |
| 4 | jl | R | M | 22.47 | 21 | 22 | 8 | |
| 5 | kp | R | F | 8.38 | 21 | 20 | 5 | |
| 6 | gp | L | M | 9.1 | 21 | 18 | 8 | |
| 7 | jo | | M | 16.56 | 19 | 22 | 6 | |
| 8 | jos | R | M | 9.21 | 19 | 20 | 5 | |
| 9 | nd | R | M | 13.39 | 19 | 19 | 6 | |
| 10 | am | R | F | 15.65 | 17 | 16 | 5 | |
| 11 | ksc | R | M | 7.41 | 17 | 12 | 4 | |
| 12 | vc | R | M | 12.09 | 24 | 21 | 6 | |
| Mean | | | | 12.4 | 20.17 | 18.50 | 5.92 | |
| Standard Deviation | | | | 4.7 | 2.08 | 2.84 | 1.16 | |
| C. Autism - Sedated | | | | | | | | |
| 1 | gd | A | M | 6.37 | 24 | 20 | 6 | 220 |
| 2 | ms | L | M | 5.81 | 23 | 21 | 5 | 200, 230 |
| 3 | ks | L | M | 7.36 | 21 | 17 | 6 | 175 |
| 4 | dp | R | M | 7.28 | 22 | 20 | 6 | 200 |
| 5 | sc | L | M | 10.9 | 20 | 18 | 5 | 200 |
| 6 | msh | R | M | 7.39 | 19 | 21 | 6 | 200 |
| 7 | dd | L | M | 7.99 | 21 | 26 | 9 | 150 |
| 8 | wh | L | M | 6.34 | 22 | 17 | 6 | 200 |
| 9 | bs | A | M | 6.18 | 22 | 17 | 5 | 200 |
| 10 | as | A | M | 5.41 | 23 | 19 | 5 | 175 |
| 11 | dh | R | M | 6.81 | 22 | 26 | 9 | 300 |
| 12 | mc | R | M | 9.59 | 23 | 20 | 5 | 225 |
| 13 | wm | A | M | 7.37 | 22 | 18 | 6 | 200 |
| 14 | av | R | M | 6.44 | 23 | 18 | 5 | 200 |
| 15 | ok | L | F | 6.23 | 23 | 20 | 5 | 200 |
| 16 | ss | A | M | 9.41 | 22 | 19 | 6 | 200 |
| 17 | jw | R | M | 7.69 | 21 | 19 | 7 | 200 |
| 18 | gw | R | M | 14.18 | 22 | 19 | 6 | 125, 150 |
| 19 | jp | R | M | 7.52 | 22 | 17 | 5 | 210 |
| 20 | fg | R | M | 8.82 | 23 | 20 | 5 | 200 |
| 21 | pd | R | M | 8.33 | 23 | 20 | 5 | 250 |
| 22 | jq | R | M | 6.6 | 20 | 15 | 6 | 200 |
| 23 | mm | R | F | 10.24 | 23 | 21 | 8 | 175 |
| 24 | mr | R | M | 6.25 | 21 | 17 | 6 | 200 |
| 25 | jk | R | M | 15.21 | 21 | 18 | 7 | 175 |
| 26 | df | R | M | 17.93 | 21 | 17 | 6 | 200 |
| 27 | pw | R | M | 6.24 | 24 | 19 | 6 | — |
| Mean | | | | 8.37 | 21.96 | 19.22 | 6 | — |
| Standard Deviation | | | | 3.05 | 1.22 | 2.47 | 1.14 | — |

All patients met DSM-IV and Autism Diagnostic Interview-Revised (ADI-R) diagnostic criteria for autism. With the ADI-R, autism is diagnosed when the subject's score is higher than a specified minimum on all three sections (social: >10; language: >8; repetitive behavior: >3). ADI-R scores did not differ between sedated and non-sedated patients for language (p=0.3168) or repetitive behaviors (p=1.0). Sedated patients were more impaired in the social domain (p<0.001). Controls were developmentally normal without siblings on the autism spectrum, performed at expected academic and social levels confirmed by scholastic performance at grade-level and parent report, and were without psychiatric conditions or psychiatric medications. Both control and autistic children were without co-morbid neurological or developmental disorders, and all medications except dietary supplements were discontinued for 2 weeks prior to the MRI examination.

fMRI Stimulation: Functional MRI scans were 2 min 29 sec in duration. A 24 sec baseline period was followed by four 15 sec presentations of speech stimulation alternating with 15 sec baseline epochs. Two scans were acquired within a total of 4 min 38 secs. Stimuli were prerecorded parents' voices presented passively via MR-safe headphones. Similar techniques using passive stimulations serve neurosurgical planning and other evaluation purposes (Souweidane M M, et al., Pediatr Neurosurg 1999; 30:86-92; Hirsch J, et al., Neurosurgery 2000; 47:711-721).

For all recordings, parents were instructed to talk about the same topics (i.e. being in the scanner, recent events, plans after the scan). Familiar voices were used to increase task compliance in younger and autistic children. Audio stimuli were power-normalized across subjects to ensure similar acoustic properties across subjects. Two independent raters judged whether the 15 sec clips of voice recordings from autistic and control parents could be distinguished. Both raters judged the child's diagnosis with only 55% accuracy (11/20) with a 43% (9/20) correspondence. Close-to-chance levels of performance indicate that narratives from autistic parents did not differ perceptibly from controls.

Imaging Procedures: Alert subjects. To minimize head-movement and distractibility, a familiar video was shown (on mute) via a rear-projection screen or via MRI compatible goggles throughout the scan. Comparisons across stimulus conditions (speech versus baseline) reveal activity related to the stimulus and not the video that occurs continuously during both stimulus and baseline epochs.

Sedated patients. Patients scanned under conventional clinical conditions using sedation received their scans for a neurologic assessment as ordered by their referring physician. Patients were induced by mask with Sevoflurane in an oxygen/nitrous oxide mixture to facilitate intravenous line (IV) placement. Once the IV was placed, patients were transitioned to an IV based anesthetic with propofol. The initial propofol dose was adjusted to render the patient motionless, but able to maintain his/her airway without an endotracheal tube. The condition of sleep produced by a steady state propofol dose was studied for one cycle of fMRI testing. Using the absence of movement artifacts on either end-tidal $CO_2$ or pulse oximetry tracings, propofol dose was reduced by 50 mcg/kg/min increments, using a technique previously described (Souweidane M M, et al., Pediatr Neurosurg 1999; 30:86-92). fMRI resumed at this lower anesthetic concentration. Scanning was stopped if gross patient movement occurred.

MRI Acquisition: Alert subjects were imaged on a research-devoted scanner and sedated patients were imaged at a clinical site within the same hospital on a comparable scanner. In both cases, a 1.5T GE Twin Speed magnetic resonance scanner was used and fMRI images were acquired using an echo planar T2*-weighted gradient echo sequence (TE=51 ms, TR=3000 ms, flip angle=83 deg). Twenty-seven contiguous axial slices covering the full brain were acquired along the AC-PC plane, with a 192×192 mm field of view (FOV) imaged on a 128×128 grid yielding an in-plane resolution of 1.56×1.56 mm and slice thickness of 4.5 mm. High-resolution structural images were acquired using a 3D SPGR sequence (124 slices, 256×256, FOV=220 mm), with a total scan time of 10 min 38 sec.

Image Analysis: Preprocessing and statistical modeling. Functional MRI images were processed using FSL 4.1 (www.fmrib.ox.ac.uk/fsl). Preprocessing consisted of brain-extraction, motion-correction, spatial smoothing (Gaussian kernel, FWHM-5 mm), high-pass filtering (cut-off=60 sec), and prewhitening. Pre-processed images were normalized to standard MNI (Montreal Neurological Institute) co-ordinate space. For statistical modeling, a first-level general linear model (GLM) was performed using one regressor which modeled the stimulus-on periods with a weight of +1 and baseline periods with a weight of 0 for each subject and each run. A second-level fixed-effects analysis was performed for the average effect across the two functional runs. Group averages were performed using FLAME 1.

Estimating custom hemodynamic response functions. Hemodynamic response functions (hrfs) were estimated for each subject using FLOBS (Woolrich, M W et al., NeuroImage, 21:4(1748-1761) 2004), a three-function basis set included in the FSL software package. Active voxels within an anatomically defined region of primary auditory cortex (A1) were selected to reconstruct the fitted hrf shape using parameter estimates for the basis functions. This technique has been used previously to estimate custom hrfs for individual subjects (Grinband J, et al., Neuroimage 2008; 43:509-520). The means of the latency was compared to the peak of the fitted hrf curves using a nonparametric Wilcoxon ranked-sum test given observed non-normal distribution of peak latency values across subjects. Mean amplitudes across 500 ms windows between 0-14 s were computed for each subject. Group comparisons at each interval were based on two-tailed independent sample t-tests, where the decision rule was set at $p<0.05$.

ROI analyses of individual subjects. Spread (n of voxels) and mean amplitude of the BOLD signal were measured in response to language-stimulation within two anatomically defined regions of interests (ROIs): primary auditory cortex (A1) and superior temporal gyrus (STG) (FIG. 1a, left), a region associated with sentence comprehension (Vigneau M, et al., Neuroimage 2006; 30(4):1414-1432; Dehaene-Lambertz G, et al., Trends Neurosci 2006; 29(7):367-373; Demonet J F, et al., Physiol Rev 2005; 85(1):49-95) with preserved activation during propofol sedation (Souweidane M M, et al., Pediatr Neurosurg 1999; 30(2):86-92; Gemma M, et al., J Neurosurg Anesthesiol 2009; 21(3):253-258; Dueck M H, et al., Acta Anaesthesiol Scand 2005; 49(6):784-791; Br J Anaesth 2004; 92(5):641-650). ROIs were computer-generated in normalized space using the Harvard-Oxford atlas probability distributions (http://www.cma.mgh.harvard.edu/) and multiplied by each subject's normalized second-level fMRI image. Contrasts between control subjects versus sedated autistic subjects and between nonsedated versus sedated and autistic subjects were run within A1 and STG ROIs.

Spread of activation within each ROI was defined as the number of voxels exceeding threshold of Z>1.6 ($p<0.05$, uncorrected). Amplitude was defined as the mean Z-score of all voxels in the specified ROI. Repeated-measures ANOVAs were performed to test main-effects and interactions between group (control vs. autism non-sedated, non-sedated autism vs. sedated autism), region (STG and A1), and hemisphere (left, right). Significant interactions were followed by post-hoc paired comparisons using two-tailed two-sample t-tests for between-group comparisons and two-tailed paired t-tests for within-group comparisons. Significance levels, p values, were Bonferroni adjusted for multiple comparisons and $p<0.05$ was the decision rule for all analyses.

To quantify the separation between individual autistic and control subjects, spread and amplitude measures were transformed to the number of standard deviations ($\sigma$) away from the mean of the control group. Subjects with $\sigma$-transformed measures below 1.0 from the control mean indicated positive for autism and those with values above this threshold indicated negative for autism. With the criterion for diagnosis of autism as −1.0 standard deviation from the control mean, specificity, sensitivity, and positive and negative predictive likelihood ratios were computed for the test. Because images for sedated healthy controls were not acquired, an estimated effect of sedation was derived by subtracting the difference between means of the sedated and non-sedated autistic subjects from the control mean, and an estimated diagnostic threshold for sedated patients was taken as one $\sigma$ (the $\sigma$ of the non-sedated control group) below this adjusted mean.

Behavioral Analysis. Mean ADI-R scores on each of three subjections (language and communication, reciprocal social interactions, and restricted, repetitive, and stereotyped behaviors and interests) were compared between sedated and nonsedated subjects by using two-sample t tests.

Results

Hemodynamic Response Function (hrf)

Figure 11A:
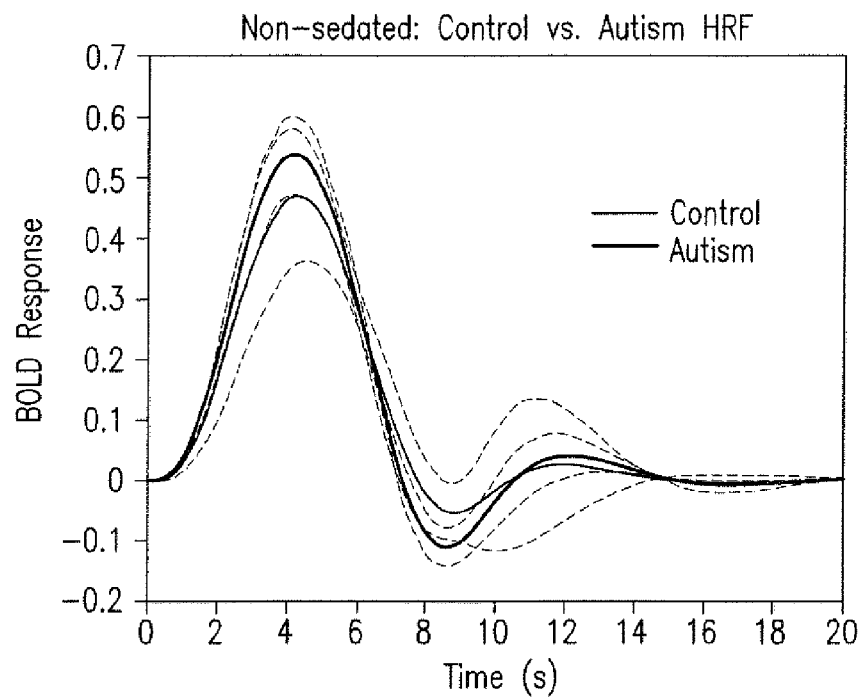
FIGS. 11a and 11b show group averaged fitted hrf functions for non-sedated control and autistic subjects (FIG. 11a), and non-sedated autistic and sedated autistic subjects (FIG. 11b). Dotted lines represent 1 standard deviation above and below the average curve.
Figure 11B:
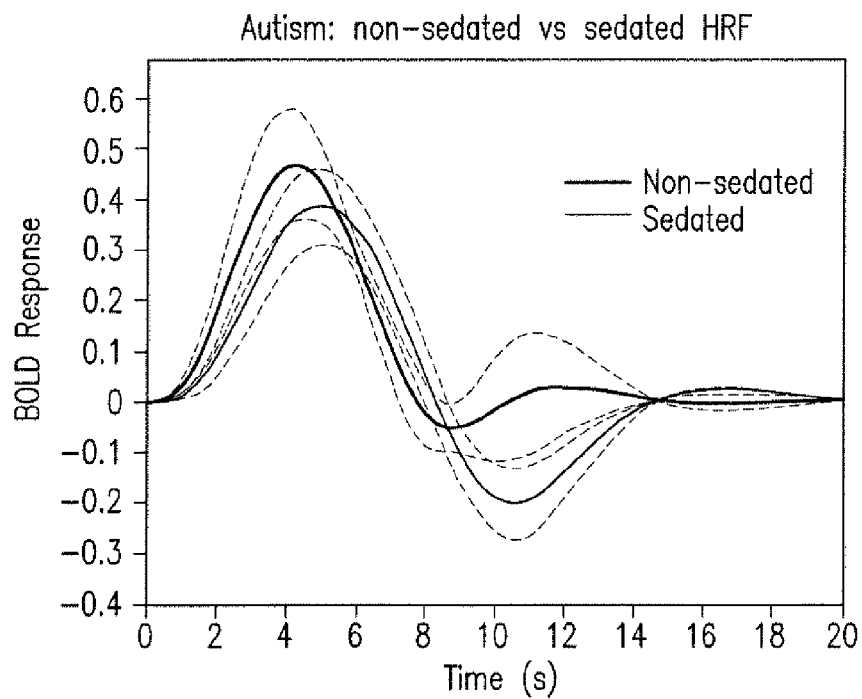

There were no differences in the shape and amplitude of the group-average fitted hrfs between autistic and control children imaged alert (FIG. 11a) and no statistical differences in time to peak (control=4.55 sec, autism=4.77 sec, p=0.92). Although the average latency to peak was about 1 s later for the sedated group relative to the non-sedated group (non-sedated=4.77 sec, sedated=5.64 sec), comparisons between non-sedated and sedated autistic patients also revealed no differences (p=0.13) (FIG. 11b). The latency at which the post-stimulus minimum occurred was also not significantly different (p=0.29). Peak amplitude of the group average curves was 4.20 sec for controls, 4.35 sec for non-sedated patients, and 5.05 sec for sedated patients. A time to peak of 5 sec is compatible with the normal adult HRF and consistent with estimates from sleeping infants (Dehaene-Lambertz G, et al., Science 2002; 298:2013-2015). There were also no significant amplitude differences between control and non-sedated autistic subjects, or between non-sedated and sedated autistic subjects.

Group fMRI Results

Figure 12A:
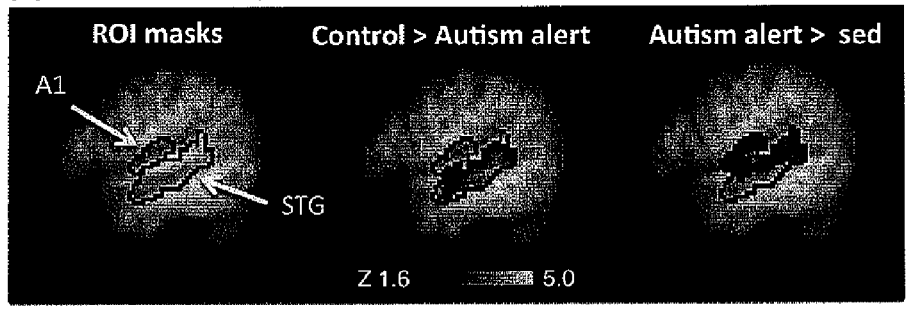
FIGS. 12a through 12c show anatomical ROIs for A1 and STG (FIG. 12a, left), Control>autism non-sedated group comparison (FIG. 12a, middle), Autism non-sedated>ASD sedated group comparison (FIG. 12a, right), Spread (FIG. 12b) and amplitude (FIG. 12c) of activation within ROIs (two-sample t-tests: **p<0.01, *p<0.05, bonferroni-adjusted).

BOLD responses were analyzed within the anatomically defined ROIs for STG and A1. Control>autism (non-sedated) group contrasts indicate greater activity in controls within STG but no difference in A1, even at the most lenient threshold of p<0.05 (FIG. 12a, middle). Non-sedated autism>sedated autism contrasts showed greater activation within both STG and A1 in non-sedated patients, p<0.05 (FIG. 12a, right).

Spread: N of Voxels

Figure 12B:
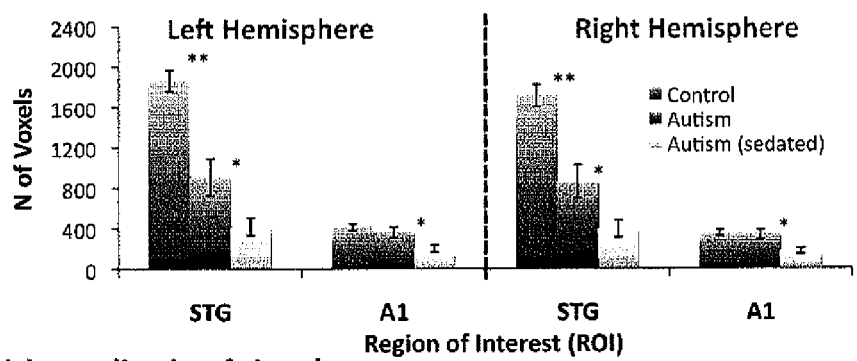

A group (control, autism)×region (STG, A1)×hemisphere (left, right) repeated-measures ANOVA indicated significant main-effect differences for group and region (Table 2A), and a group×region interaction, $F(1,11)=18.176$, $p<0.001$ for spread of the BOLD signal within each ROI. Paired comparisons revealed larger spread for control subjects relative to non-sedated autistic subjects in STG bilaterally (both left and right, p<0.001) but not in A1 (p<1.0) (FIG. 12b, unshaded and shaded bars). A similar ANOVA comparing non-sedated and sedated autistic patients indicated significant main effects for group and region (Table 3b) as well as a group×region interaction, $F(1,11)=4.931$, $p<0.048$. Paired comparisons revealed larger spread for non-sedated patients relative to sedated patients in bilateral STG (p<0.03) and A1 (left, p<0.049; right, p<0.011) (FIG. 12a, shaded and hatched bars).

Amplitude of Signal Strength: Mean Z-Score

Figure 12C:
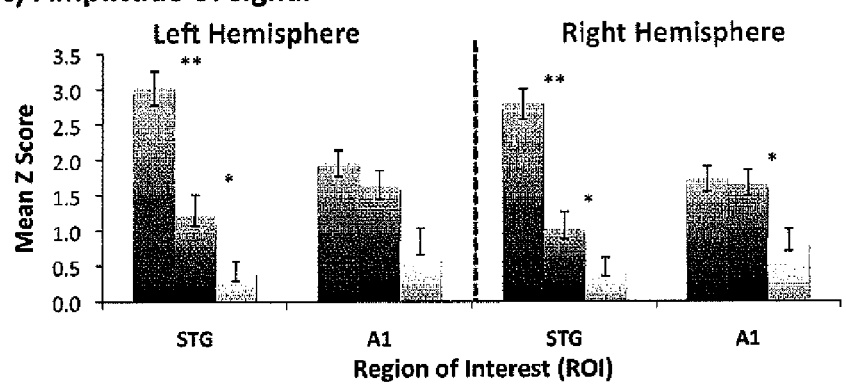

Comparisons of signal amplitude showed similar results to those observed for spread (above). A group (control, autism)×region (STG, A1)×hemisphere (left, right) repeated-measures ANOVA indicated significant main-effect differences for group and region (Table 2c) and a significant group×region interaction, $F(1,11)=20.19$, $p<0.001$. Paired-comparisons revealed greater mean amplitude in controls relative to autistic subjects in bilateral STG (p<0.001) but not in A1 (p<1.0) (FIG. 12b, unshaded and shaded bars). A similar ANOVA between non-sedated and sedated autistic patients indicated significant main effects for group and region (Table 2d). Paired comparisons revealed greater activation in bilateral STG (left p<0.04, right, p<0.05) and in right A1 (p<0.02), but not in left A1 (p<0.07) in non-sedated relative to sedated patients (FIG. 12c, shaded and hatched bars).

Differentiation Between Autistic and Control Subjects

Figure 13A:
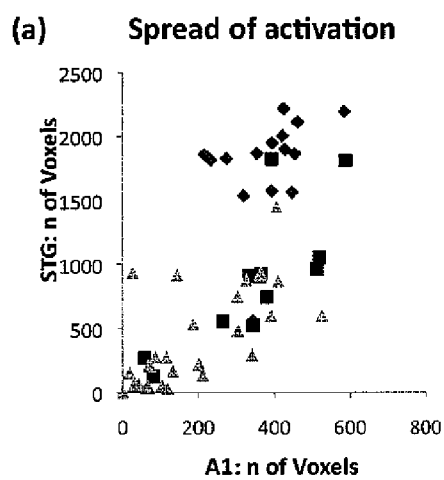
FIGS. 13a and 13b show individual measures for spread (FIG. 13a) and amplitude (FIG. 13b) in STG (y-axis) and A1 (x-axis). Control and autism groups are separated along the STG (y)-axis and not along the A1 (x)-axis. Values are averaged across hemispheres.
Figure 13B:
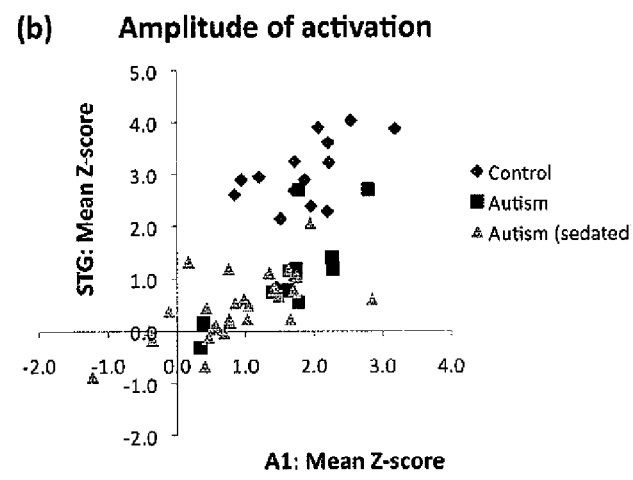

Plots of voxel count (spread, FIG. 13a) and Z score (amplitude, FIG. 13b) of individual control (square symbols) and autistic subjects (triangular and circular symbols) for STG (y-axis) against A1 (x-axis) confirm the separation between groups for STG but not for A1. Because there were no significant differences between hemispheres in all groups (Table 2), these results were collapsed across hemisphere.

TABLE 2

ANOVA: 2 Group × 2 Region × 2 Hem

| | F(1, 11) | p |
|---|---|---|
| Spread: n of Voxels | | |
| (a) Control V Autism | | |
| Group | 13.909 | 0.003 * |
| Region | 307.833 | <0.001 * |
| Hem | 3.479 | 0.89 |
| Grp * Reg | 18.176 | 0.001 * |
| Grp * Hem | 0.387 | 0.55 |
| Reg * Hem | 0.689 | 0.42 |
| Grp * Reg * Hem | 0.202 | 0.66 |
| (b) Non V Sed | | |
| Group | 11.631 | 0.006 * |
| Region | 21.958 | 0.001 * |
| Hem | 0.351 | 0.57 |
| Grp * Reg | 4.931 | 0.05 * |
| Grp * Hem | 0.053 | 0.82 |
| Reg * Hem | 0.006 | 0.94 |
| Grp * Reg * Hem | 0.133 | 0.72 |
| Amplitude: Mean Z-score | | |
| (c) Control V Autism | | |
| Group | 13.15 | 0.004 * |
| Region | 20.116 | 0.001 * |
| Hem | 3.709 | 0.08 |
| Grp * Reg | 20.192 | 0.001 * |
| Grp * Hem | 0.265 | 0.62 |
| Reg * Hem | 1.855 | 0.20 |
| Grp * Reg * Hem | 0.014 | 0.91 |
| (d) Non V Sed | | |
| Group | 10.427 | 0.008 * |
| Region | 11.846 | 0.006 * |
| Hem | 0.183 | 0.677 |
| Grp * Reg | 0.198 | 0.665 |
| Grp * Hem | 0.354 | 0.564 |
| Reg * Hem | 0.363 | 0.559 |
| Grp * Reg * Hem | 0.819 | 0.385 |

Figure 14A:
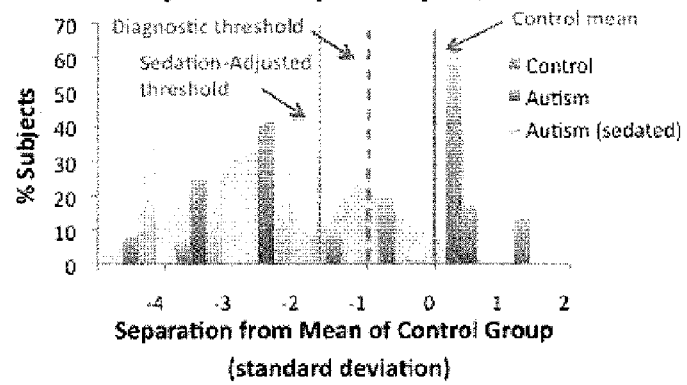
FIGS. 14a and 14b show recent subjects (controls; non-sedated autism; sedated autism) whose values for (a) spread and (b) amplitude fell within 1-3 SDs from the control mean (solid-lines). Threshold for diagnostic was set to 1 SD below the control mean (dashed-lines).
Figure 14B:
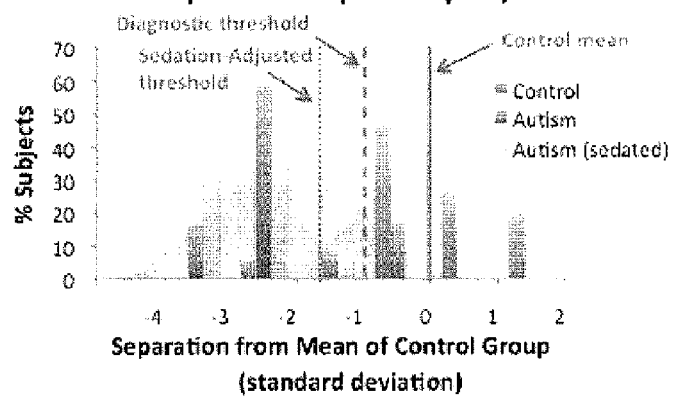

The extent to which differences in the spread and amplitude of activation in STG separated patients and controls can be quantified by the degree of overlap across the groups (FIG. 14). The percentage of sedated (hatched) and non-sedated (shaded) autistic subjects and controls (unshaded) that fell within one to four standard deviations ($\sigma$) from the control mean (solid line) are shown for spread (FIG. 14a) and amplitude (FIG. 14b). For both spread and amplitude, 83% of non-sedated autistic subjects fell below 1 SD of the control mean, whereas only 7% of control subjects fell in that region. Thus, a diagnostic threshold for autism as one $\sigma$ below the control mean (FIG. 13, dashed lines) for both measures was defined. For non-sedated subjects, the sensitivity (proportion of true positives) of this test is 83% (CI=±21.1) and the specificity (proportion of true negatives) is 93% (CI=±12.6). The positive likelihood ratio, LR, (number of true positives to false positives) is 12.5 and the negative likelihood ratio, LR, (number of true negatives to false negatives) is 5.6.

Because of the unavailability of sedated healthy volunteer children, the sensitivity of a similar test for sedated autistic patients was estimated by adjusting the diagnostic threshold by the effect of sedation between non-sedated and sedated autistic patients (FIG. 14, dotted lined). The sensitivity of a test based on this adjusted threshold for sedated autistic patients is 85% (CI=±11.3) for spread and 96% (CI=±7.12) for amplitude.

Discussion

This study establishes that fMRI activation within language-sensitive brain regions during passive speech stimulation distinguishes between language impaired autistic and age-matched control children. Two measures were identified, signal spread and amplitude, using anatomically defined ROIs applied to individual patterns of activation. A standard atlas was chosen to define two ROIs (A1 and STG) to provide a systematic and automated method (Bohland J W, et al., PLOS One 2009; 4:e7200) transferable to standard clinical practice. Differences in activation in STG, but not A1, suggest intact auditory processing but disrupted linguistic comprehension at higher processing stages. Both spread and amplitude of activation within STG was greater for control children relative to autistic patients imaged alert, whereas A1 showed no difference, consistent with previous studies using passive stimulation paradigms such as employed here that report decreased activation in the temporal lobe in autistic subjects (Gervais H, et al., Nat Neurosci 2004, 7:801-802; Muller R A, et al., J Autism Dev Disord 1999, 29:19-31; Boddaert N, et al., Am J Psychiatry 2004, 161:2117-2120). Structural MR imaging studies have also reported atypical laterality of temporal lobe brain volume in groups of autistic adults and children (Jou R J, et al., Brain Res 2010; 1360:205-212; Rojas D C, et al., J Autism Dev Disord 2005; 35(4):479-486). The present study extends previous reports of group-level differences and suggests that individual functional MR imaging measures of spread and amplitude can be used to differentiate autistic from nonautistic subjects. In practice, only one measure (spread or amplitude) would be sufficient. Optimal diagnostic criteria, however, will require future studies.

A major obstacle to imaging children in functional studies includes task compliance, tolerance of the scanning environment, and maintenance of a steady head position for sufficient durations of time. To image children while alert, a "silent video" was employed to overcome these obstacles. However, patients who could not tolerate the scanner environment even under these optimized circumstances and for whom a conventional scan was indicated, were imaged under clinical management and propofol sedation, a technique that offers an effective alternative enabling functional images in young children (Souweidane M M, et al, Pediatr Neurosurg 1999, 30:86-92; Altman N R, Bernal B., Radiology 2001, 221:56-63; Gemma M, et al., 2009, 21:253-258; Bernal B, Altman N R., Radiology 2003, 229:651-658). If fMRI is to be applied as a diagnostic tool for use with children with developmental delay, sedation would likely be necessary in most cases.

Sedated autistic patients showed overall decreases in spread and amplitude of signal in both temporal regions (A1 and STG) relative to non-sedated patients, consistent with fMRI studies in sedated adults and children (Bernal B, Altman N R., Radiology 2003, 229:651-658; Dueck M H, et al., Acta Anaesthesiol Scand 2005, 49:784-791; Heinke W, et al., Br J Anaesth 2004, 92:641-650; Davis M H, et al., Proc Natl Acad Sci USA 2007, 104:16032-16037). Although healthy control subjects imaged under sedation were not included, a test derived from adjusted threshold values based on the effect of sedation between non-sedated and sedated autistic subjects showed similarly high sensitivity estimates for the diagnosis of sedated autistic children. Patients without autism or developmental delay undergoing MR imaging under sedation may serve as a possible control group in future studies. Differential patterns of brain activation have also been previously described in children with language delay imaged under sedation (Bernal B, Altman N R. Radiology 2003, 229:651-658). The observation that the time to peak of the hrf is similar between autistic and control children imaged alert, and between autistic subjects imaged alert and under sedation, indicates that sedation does not differentially affect this fundamental property of the BOLD signal. These findings are consistent with previous studies that optimally modeled fMRI responses to language stimuli using the canonical hrf in sleeping and sedated children with and without developmental delay (Altman N R, Bernal B., Radiology 2001, 221:56-63; Gemma M, et al., J Neurosurg Anesthesiol 2009, 21:253-258; Dehaene-Lambertz G, et al., Science 2002, 298:2013-2015).

The mean age of sedated subjects in the study was less than that of non-sedated subjects. However, it is unlikely that observed differences between sedated and nonsedated subjects in the present study are due to age, as previous studies in typically developing infants as young as three months have shown activation in STG to passive language stimulation (Dehaene-Lambertz G, et al., Science 2002; 298(5600):2013-2015; Dehaene-Lambertz G, et al., Proc Natl Acad Sci USA 2006; 103(38):14240-14245). Furthermore, limitations associated with the quantification of functional MR imaging signals include the choice of an appropriate threshold because activation patterns will change depending on threshold. At present, a most liberal threshold of significance, $p<0.05$ ($z>1.6$), was selected for comprehensive assessment.

The application of fMRI to determine physiological differences between autism and control children may be investigated in future studies to distinguish between autism and other developmental disorders such as specific language impairment. Given the concern over the extent to which these disorders are etiologically distinct (Bishop D V. Autism, Br J Disord Commun 1989, 24:107-121; Williams D., et al., Psychol Bull 2008, 134:944-963; Bishop D V, et al., J Child Psychol Psychiatry 2002, 43:917-929), an objective biomarker to distinguish between these disorders might be used to shape the diagnostic criteria. Because the present study did not include subjects with abnormalities other than autism, our findings cannot be used to differentiate autism from other causes of developmental delay. These findings complement a recent study using MRI and pattern recognition techniques to identify subtle differences in neuroanatomical features between autistic, control, and ADHD subjects (Ecker C., et al., J Neurosci 2010, 30:10612-10623) and support the potential use of neurophysiological measurements for diagnosis. Furthermore, although correlations between the degree of behavioral impairment and functional MR imaging measures were not observed in the present study, possibly due to limited sample variability, future studies including patients with varying levels of disability along the autism spectrum may help establish a relationship between these measures. If so, functional MR imaging may serve as a neural measure of change in function following medical or neuropsychological intervention.

The subjects included in this report participated in a group study not designed specifically to determine the diagnostic value of fMRI. Thus, limitations to these conclusions include the question of age and how these findings would apply to younger children, when an objective medical diagnostic would be most useful for the purpose of early intervention. Despite limitations related to the age of the sample and the lack of a sedated control group, the present finding that fMRI can be employed to differentiate language impaired autistic children from control children at older ages suggests the benefit of larger-scale studies to investigate the use of measures established here as a test for early detection of autism and other developmental disorders.

* * *

The foregoing merely illustrates the principles of the disclosed subject matter. Various modifications and alterations to the described embodiments will be apparent to those skilled in the art in view of the inventors' teachings herein. Features of existing methods can be seamlessly integrated into the methods of the exemplary embodiments of the disclosed subject matter or a similar method. It will thus be appreciated that those skilled in the art will be able to devise numerous methods which, although not explicitly shown or described herein, embody the principles of the disclosed subject matter and are thus within its spirit and scope.

Patents, patent applications, publications, procedures, and the like are cited throughout this application, the disclosures of which are incorporated herein by reference in their entireties.

What is claimed is:

1. A method of determining whether a test subject suffers from an autism disorder using one or more test subject brain images obtained by a combination of functional MRI and DTI imaging techniques, comprising:

comparing the one or more test subject brain images from a functional MRI imaging technique to one or more corresponding control subject brain images to identify one or more locations in the test subject's brain sensitive to passive auditory stimulation, wherein the one or more test subject brain images from the functional MRI imaging technique show hypoactivity in at least one location of the test subject's brain selected from the group consisting of superior temporal gyrus, left inferior frontal gyrus, and left medial frontal gyrus;

comparing the one or more test subject brain images from a DTI imaging technique to one or more corresponding control subject brain images to identify one or more locations in the test subject's brain sensitive to passive auditory stimulation, wherein the one or more test subject brain images from the DTI imaging technique show hypoactivity in at least one location of the test subject's brain selected from the group consisting of uncinate fasciculus, the arcuate fasciculus, the left superior temporal gyrus, and the left inferior frontal gyrus; and correlating the one or more test subject brain images from the functional MRI imaging technique of the test subject's brain with the one or more test subject brain images from the DTI imaging technique of the test subject's brain to identify an autism spectrum disorder.

2. The method of claim 1, wherein the passive auditory stimulation comprises one or more stimuli selected from the group consisting of speech, reverse speech, instrumental music, song with lyrics, and song without lyrics.

3. The method of claim 2, wherein the passive auditory stimulation comprises alternating periods of audio clips and silence.

4. The method of claim 3, wherein the alternating periods comprise same time duration.

5. The method of claim 3, wherein the alternating periods comprise different time duration.

6. The method of claim 1, wherein the passive auditory stimulation includes speech.

7. The method of claim 6, wherein the one or more test subject brain images obtained from the functional MRI imaging technique include images indicative of sparse frontal lobe activity of the test subject's brain.

8. The method of claim 6, wherein the one or more test subject brain images obtained from the functional MRI imaging technique include images indicative of sparse superior temporal gyrus activity of the test subject's brain.

9. The method of claim 7, wherein the one or more test subject brain images obtained from the DTI imaging technique include images indicative of compromised integrity of connectivity from Wernicke's Area to Broca's Area of the test subject's brain.

10. The method of claim 7, wherein the one or more test subject brain images obtained from the DTI imaging technique include images indicative of a reduced fractional anisotropy value of the arcuate fasciculus of the test subject's brain.

11. The method of claim 1, wherein the subject is sedated.

* * * * *